United States Patent
Agris

(10) Patent No.: US 10,266,527 B2
(45) Date of Patent: Apr. 23, 2019

(54) T-BOX RIBOSWITCH-BINDING ANTI-BACTERIAL COMPOUNDS

(71) Applicant: THE RESEARCH FOUNDATION FOR THE STATE UNIVERSITY OF NEW YORK, Albany, NY (US)

(72) Inventor: Paul F. Agris, Albany, NY (US)

(73) Assignee: THE RESEARCH FOUNDATION FOR THE STATE UNIVERSITY OF ALBANY, Albany, NY (US)

( * ) Notice: Subject to any disclaimer, the term of this patent is extended or adjusted under 35 U.S.C. 154(b) by 0 days.

(21) Appl. No.: 14/907,138

(22) PCT Filed: Jul. 23, 2014

(86) PCT No.: PCT/US2014/047859
§ 371 (c)(1),
(2) Date: Jan. 22, 2016

(87) PCT Pub. No.: WO2015/013431
PCT Pub. Date: Jan. 29, 2015

(65) Prior Publication Data
US 2016/0194317 A1 Jul. 7, 2016

Related U.S. Application Data

(60) Provisional application No. 61/857,492, filed on Jul. 23, 2013.

(51) Int. Cl.
| | | |
|---|---|---|
| C07D 471/04 | (2006.01) |
| C07D 215/56 | (2006.01) |
| C07D 491/147 | (2006.01) |
| C07D 277/46 | (2006.01) |
| C07D 417/04 | (2006.01) |
| A61K 31/4745 | (2006.01) |
| A61K 45/06 | (2006.01) |
| A61K 31/496 | (2006.01) |
| A61K 31/426 | (2006.01) |
| A61K 31/427 | (2006.01) |
| C07C 233/06 | (2006.01) |
| A61K 31/47 | (2006.01) |
| C07D 215/20 | (2006.01) |
| A61K 31/196 | (2006.01) |
| C07D 471/06 | (2006.01) |
| C07D 491/052 | (2006.01) |

(52) U.S. Cl.
CPC .......... *C07D 471/04* (2013.01); *A61K 31/196* (2013.01); *A61K 31/426* (2013.01); *A61K 31/427* (2013.01); *A61K 31/47* (2013.01); *A61K 31/4745* (2013.01); *A61K 31/496* (2013.01); *A61K 45/06* (2013.01); *C07C 233/06* (2013.01); *C07D 215/20* (2013.01); *C07D 215/56* (2013.01); *C07D 277/46* (2013.01); *C07D 417/04* (2013.01); *C07D 471/06* (2013.01); *C07D 491/052* (2013.01); *C07D 491/147* (2013.01); *C07C 2601/14* (2017.05); *C07C 2602/42* (2017.05)

(58) Field of Classification Search
None
See application file for complete search history.

(56) References Cited

U.S. PATENT DOCUMENTS

| | | |
|---|---|---|
| 6,537,774 B1 | 3/2003 | Huang et al. |
| 2009/0325948 A1 | 12/2009 | Hurley et al. |
| 2012/0283219 A1 | 11/2012 | Coish et al. |

FOREIGN PATENT DOCUMENTS

| | | | |
|---|---|---|---|
| JP | 2005097195 | * | 4/2005 |
| JP | 2005097195 MT | * | 4/2005 |

OTHER PUBLICATIONS

Goodman and Gilman's The Pharmacological Basis of Therapeutics (Tenth Edition (2001), McGraw Hill, Chapter I, pp. 3-29.*
International Search Report for PCT/US14/47859 dated Dec. 9, 2014.

* cited by examiner

*Primary Examiner* — Dennis Heyer
(74) *Attorney, Agent, or Firm* — Heslin Rothenberg Farley & Mesiti P.C.

(57) ABSTRACT

The present disclosure identifies compounds that bind to a t-RNA-dependent riboswitch of aaRS gene expression unique to Gram-positive bacteria. The compounds have anti-bacterial activity.

17 Claims, 13 Drawing Sheets

T-BOX RIBOSWITCH-BINDING ANTI-BACTERIAL COMPOUNDS

CROSS REFERENCE TO RELATED APPLICATIONS

This application is a national phase filing under 35 U.S.C. § 371 of PCT International Application No. PCT/US2014/047859, filed on Jul. 23, 2014, which claims priority to U.S. Provisional application Ser. No. 61/857,492 filed Jul. 23, 2014; the contents of both are incorporated by reference into the present application.

TECHNICAL FIELD

The present invention generally relates to antibacterial agents. More particularly, the present invention relates to compounds with bactericidal/bacteriostatic activity against Gram-positive organisms.

BACKGROUND OF THE INVENTION

As is the case with many Gram-positive pathogens including bacilli and streptococci, staphylococci cause endemic, drug resistant infections over time, for which there are few effective therapeutics. Vancomycin, often considered the last line of defense against methicillin-resistant *staphylococcus aureus* (MRSA), is now demonstrating an all too familiar path of decreasing effectiveness against rapidly mutating *S. aureus*. Therefore, there is a critical need for new antibiotics refractory to common resistance mechanisms.

The current arsenal of antibacterial drugs targets only a very narrow spectrum of cellular processes. In particular, a survey recently discovered that antibiotic drug development has produced only one new chemical scaffold in the past 30 years, and that currently prescribed antibiotics collectively disrupt the function of only four bacterial life processes [4]. As a consequence, antibiotic resistance is now emerging at an alarmingly rapid pace, and the most recently approved antibiotics could soon be ineffective [5]. Sustained success in the long-term battle against bacterial pathogens, including MRSA, will require the identification of new chemical scaffolds that target new cellular processes.

Among identified RNA targets, the riboswitch motif has attracted increasing attention. Riboswitches are new, validated targets for novel small molecule intervention against MRSA and other pathogens.[75] Riboswitches, functional structures within the 5'-untranslated region (5'UTR) of messenger RNA (mRNA), regulate gene expression in bacteria. Riboswitches are highly selective RNA receptors for the many metabolites that act as cues to control the needs of the organism through termination of transcription or initiation of translation. The conformational change that the riboswitch incurs upon the binding of the metabolite ligand affects the transcription or translation event. Thus, an analog of the natural metabolite could control expression of an essential gene in such a way as to be lethal to the pathogen.[75] Other types of riboswitches have a ligand-activated, self-cleavage mechanism that destabilizes the mRNA speeding turnover.[76] Eukaryotic riboswitches activate alternative splicing as a means of controlling gene expression in response to ligand binding. Some bacterial riboswitches are similarly capable.[76] Therefore, most riboswitches of bacterial pathogens are unique targets of intervention that do not occur in the host. Rational drug design of small molecule, ligand analogs can be, and have been, pursued against MRSA and other pathogens with the determination of the 3D-structures of the bound and free fragments of mRNA 5'UTR riboswitch.[76]

RNA molecules offer significant advantages as drug targets as compared to proteins. As there are far fewer copies of mRNA than protein products, significantly less drug would be required to produce an effect and the mRNA offers a target site relatively more refractory to resistance than that of a traditional protein target. With an insidious pathogen such as MRSA being isolated in war wounds, the importance of identifying new drugs and new drug targets against this multi-drug resistant pathogen cannot be overstated.

SUMMARY OF THE INVENTION

The present disclosure provides compounds which target a T-box riboswitch in bacteria and have anti-bacterial activity, that is, are either bactericidal or bacteriostatic.

In one aspect, the invention relates to a compound of Formula (I)

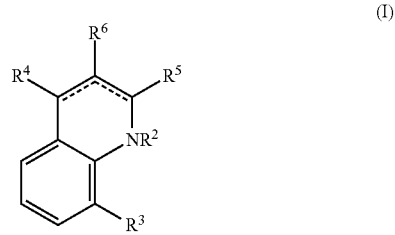

(I)

or a pharmaceutically acceptable salt thereof, wherein:
$R^2$ is selected from hydrogen and $C_{1-6}$ alkyl;
$R^3$ is hydrogen;
or $R^2$ and $R^3$, together with the nitrogen and carbon atoms to which they are respectively attached, form a fused heterocyclic ring having 5 or 6 ring members of which up to 2 can be heteroatoms selected from N, O, and S;
$R^4$ and $R^5$ are independently selected from —$OR^7$ and oxo, provided that at least one of $R^4$ and $R^5$ is —$OR^7$, and at least one of $R^4$ and $R^5$ is oxo;
═══ represents a single or double bond, wherein the ═══ joining the ring carbon attached to $R^6$ and the ring carbon atom attached to a —$OR^7$ group is a double bond, and wherein the ═══ joining the carbon attached to $R^6$ and the carbon atom attached to an oxo group is a single bond;
$R^6$ is —C(═O)NH(CH)$_n$NR$^8$R$^9$;
$R^7$ is hydrogen,
or $R^6$ and $R^7$, and together with the carbon and oxygen atoms to which they are respectively attached, form a fused heterocyclic 6-membered ring containing, as the single ring heteroatom, the oxygen to which $R^7$ is attached, and wherein said fused heterocyclic 6-membered ring is optionally substituted with one to three substituents individually selected from hydroxy and oxo;
n is 1, 2, 3, or 4; and
$R^8$ and $R^9$ are individually selected from hydrogen, $C_{1-3}$ alkyl, and hydroxy $C_{1-3}$ alkyl, or Fe and $R^9$, together with the nitrogen atom to which they are attached, form a fused piperazine ring.

In one embodiment of a compound of Formula (I), $R^2$ and $R^3$, together with the nitrogen and carbon atoms to which they are respectively attached, form a fused heterocyclic ring having 5 or 6 ring members, wherein the only heteroatom in said fused heterocyclic ring is the nitrogen atom to which $R^2$ is attached.

In a particular embodiment, n is 2.

In one embodiment, the compound of Formula (I) is a compound of Formula (Ia):

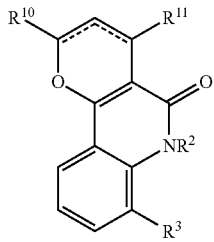
(Ia)

wherein $R^{10}$ and $R^{11}$ are individually selected from hydroxy and oxo, provided that at least one of $R^{10}$ and $R^{11}$ is hydroxy, and at least one of $R^{10}$ and $R^{11}$ is oxo; and ==== represents a single or double bond, wherein the ==== attached to the ring carbon atom attached to a hydroxyl group is a double bond, and wherein the ==== attached to the ring carbon atom attached to an oxo group is a single bond.

In some embodiments, the compound of Formula (I) is a compound of Formula (Ib-If):

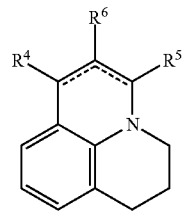
(Ib)

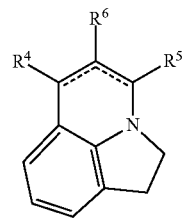
(Ic)

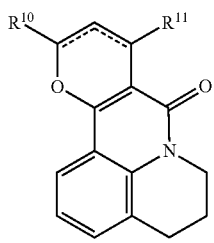
(Id)

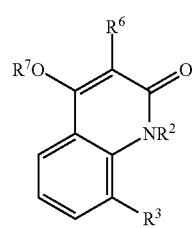
(Ie)

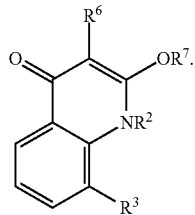
(If)

In another aspect, the invention relates to compositions comprising a compound of Formula I and use of those compounds and compositions to inhibit Gram-positive bacterial growth and treat or prevent infection caused by Gram-positive bacteria.

In a related aspect, therefore, the invention relates to a method for killing or inhibiting the growth of Gram-positive bacteria comprising contacting the bacteria with a compound of formula I:

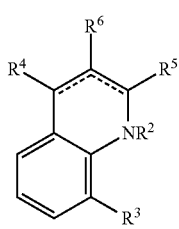
(I)

or a pharmaceutically acceptable salt thereof, wherein:

$R^2$ is selected from hydrogen and $C_{1-6}$ alkyl;

$R^3$ is hydrogen;

or $R^2$ and $R^3$, together with the nitrogen and carbon atoms to which they are respectively attached, form a fused heterocyclic ring having 5 or 6 ring members of which up to 2 can be heteroatoms selected from N, O, and S;

$R^4$ and $R^5$ are independently selected from $-OR^7$ and oxo, provided that at least one of $R^4$ and $R^5$ is $-OR^7$, and at least one of $R^4$ and $R^5$ is oxo;

==== represents a single or double bond, wherein the ==== joining the ring carbon attached to $R^6$ and the ring carbon atom attached to a $-OR^7$ group is a double bond, and wherein the ==== joining the carbon attached to $R^6$ and the carbon atom attached to an oxo group is a single bond;

$R^6$ is $-C(=O)NH(CH)_n NR^8 R^9$;

$R^7$ is hydrogen, or $R^6$ and $R^7$, and together with the carbon and oxygen atoms to which they are respectively attached, form a fused heterocyclic 6-membered ring containing, as the single ring heteroatom, the oxygen to which $R^7$ is attached, and wherein said fused heterocyclic 6-membered ring is optionally substituted with one to three substituents individually selected from hydroxy and oxo;

n is 1, 2, 3, or 4; and $R^8$ and $R^9$ are individually selected from hydrogen, $C_{1-3}$ alkyl, and hydroxy $C_{1-3}$ alkyl, or $R^8$ and $R^9$, together with the nitrogen atom to which they are attached, form a fused piperazine ring.

where $R_1$ and $R_4$ are independently carbonyl or hydroxyl;

$R_2$ and $R_3$ are independently H or $C_{1-4}$ alkyl or, taken together $R_2$ and $R_3$ form a six-membered carbocyclic ring; and X is $(CH_2)_n$ wherein n is 1-5 and one $(CH_2)$ may optionally be replaced by NH, provided that said NH is not at the point of attachment to the piperazine.

In another aspect, the invention relates to a compound of Formula II

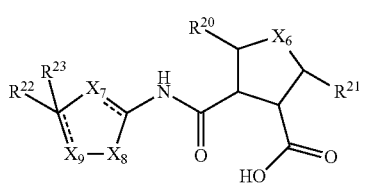

(II)

or a pharmaceutically acceptable salt thereof, wherein:
$X_6$ is selected from $CH_2$ and $—CR^{24}\!\!=\!\!CR^{25}—$;
$X_7$ is selected from nitrogen and $CH_2$;
$X_8$ is selected from sulfur and $CH_2$;
$X_9$ is selected from $CR^{24}$ and $—CHR^{24}—CHR^{25}—$;
═ represents a single or double bond, wherein both instances of ═ are double bonds when $X_7$ and $X_8$ are nitrogen and sulfur, respectively, and both instances ═ are single bonds when $X_7$ and $X_8$ are both $CH_2$;
$R^{20}$ and $R^{21}$ are individually selected from hydrogen and $C_{1-3}$ alkyl, or $R^{20}$ and $R^{21}$, taken together, represent a $—CH_2—CH_2—$ linker;
$R^{22}$ is selected from hydrogen, $C_{1-3}$ alkyl, and a 5- or 6-membered aryl or heteroaryl ring, wherein said 5- or 6-membered aryl or heteroaryl ring is optionally substituted with 1, 2, or 3 substituents individually selected from $C_{1-6}$ alkyl and halogen;
$R^{23}$ is absent or is selected from hydrogen and $C_{1-3}$ alkyl; and
$R^{24}$ and $R^{25}$ are individually selected from hydrogen and $C_{1-3}$ alkyl.

In some embodiments of compounds of Formula (II), $R^{20}$ and $R^{21}$, taken together, represent a $—CH_2—CH_2—$ linker.

In some such embodiments, $X_6$ is $CH_2$, such that the ring

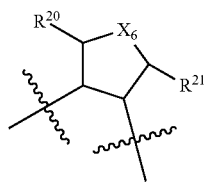

represents a norbornane,

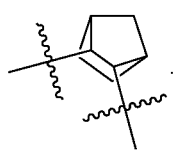 [SMILES: *C1C2CCC(C2)C1*]

In some embodiments, $R^{22}$ is selected from optionally substituted phenyl and optionally substituted thienyl.

In some embodiments, $R^{22}$ is a 5- or 6-membered aryl or heteroaryl ring substituted with two halogen atoms. In some embodiments, the halogen atoms are selected from fluorine and chlorine.

In some embodiments, the compound of Formula (II) is a compound of Formula (IIa-IId):

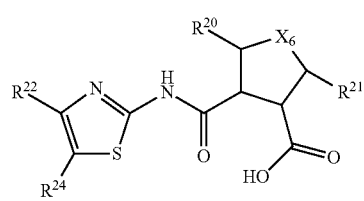

(IIa)

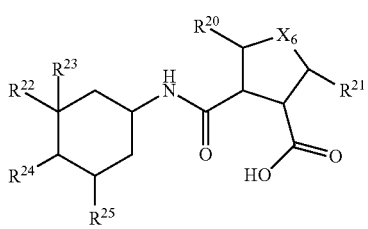

(IIb)

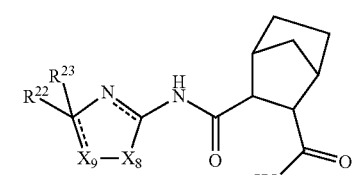

(IIc)

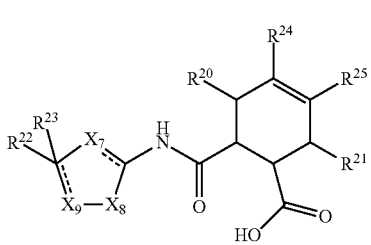

(IId)

The present invention further relates to compositions comprising the compound of Formula II and use of said compounds and compositions to inhibit Gram-positive bacterial growth and treat or prevent infection caused by Gram-positive bacteria.

In a related aspect, the invention relates to a method for killing or inhibiting the growth of Gram-positive bacteria comprising contacting the bacteria with a compound of formula II.

These and other objects, features and advantages of this invention will become apparent from the following detailed description of the various aspects of the invention taken in conjunction with the accompanying drawings.

DETAILED DESCRIPTION OF THE INVENTION

Figure 1:
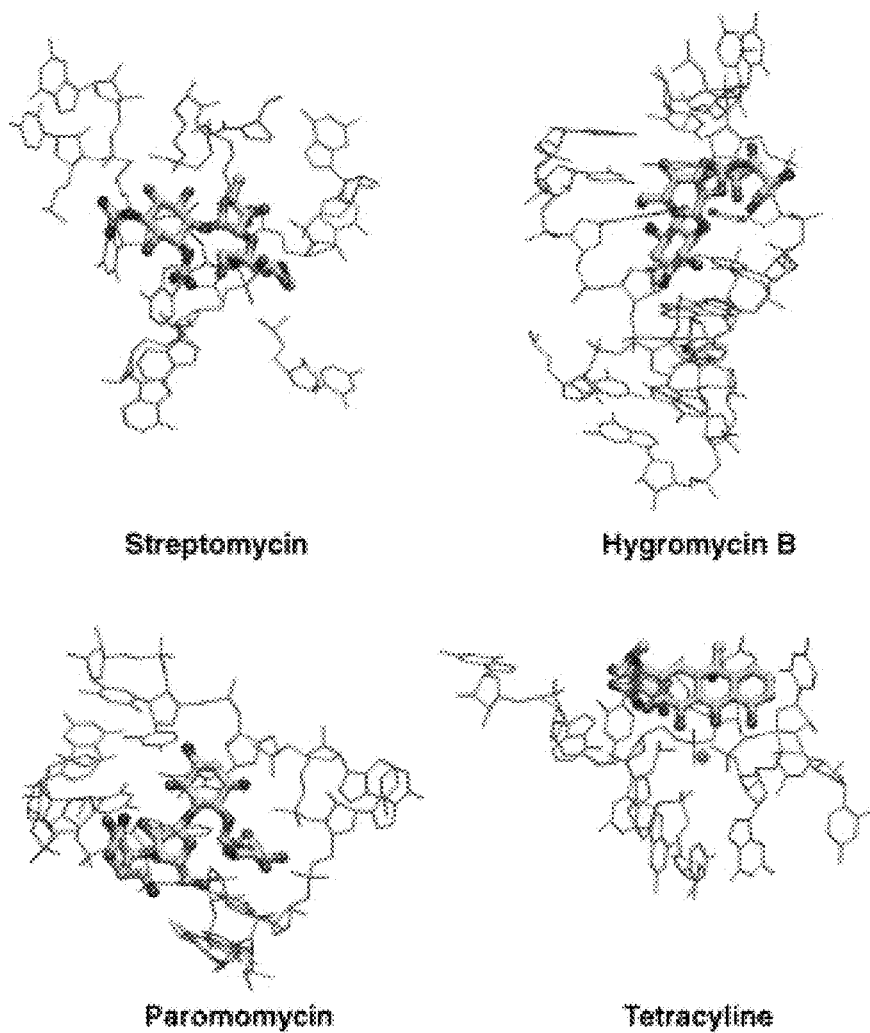
FIG. 1 shows the diversity of antibiotic binding modes to the ribosome RNAs. Antibiotics are shown as ball-and-stick representations; nucleotides, amino acids and magnesium ions are shown in grey, red and green, respectively. Adapted from Vicens and Westhof [13].

All patents, publications, applications and other references cited herein are hereby incorporated by reference into the present application.

As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, which are herein incorporated by reference in their entirety.

Unless otherwise specified, alkyl is intended to include linear, branched, and cyclic hydrocarbon structures and combinations thereof. A combination would be, for example, cyclopropylmethyl. $C_{1-6}$alkyl groups are those having one to six carbon atoms. Examples of $C_{1-6}$ alkyl groups include methyl, ethyl, propyl, isopropyl, butyl, s- and t-butyl and the like. Cycloalkyl (which includes cyclic hydrocarbon groups) is a subset of alkyl. Examples of cycloalkyl groups include c-propyl, c-butyl, c-pentyl, norbornyl and the like.

Aryl and heteroaryl ring systems mean (i) a phenyl group (or benzene) or a monocyclic 5- or 6-membered heteroaromatic ring containing 1-4 heteroatoms selected from O, N, and S; (ii) a bicyclic 9- or 10-membered aromatic or heteroaromatic ring system containing 0-4 heteroatoms selected from O, N, and S; or (iii) a tricyclic 13- or 14-membered aromatic or heteroaromatic ring system containing 0-5 heteroatoms selected from O, N, and S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene (thiene), benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

The term "halogen" (or "halo") means fluorine, chlorine, bromine or iodine. In one embodiment, halogen may be fluorine or chlorine.

The term "heterocyclic group" includes within its scope aromatic, non-aromatic, unsaturated, partially saturated and fully saturated heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. A particular non-limiting example is a morpholinyl group.

Radicals and substituents ($R^e$) are generally defined when introduced and retain that definition throughout the specification and in all independent claims.

The salt forms of the compounds of formulas (I), (II), and (III) are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts.

The term "pharmaceutically acceptable salt" refers to salts prepared from pharmaceutically acceptable non-toxic acids or bases including inorganic acids and bases and organic acids and bases. When the compounds used in the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for compounds that may be used in the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Where the compounds of formulae herein contain an amine function, some may form quaternary ammonium salts, for example by reaction with an alkylating agent according to methods well known to persons having ordinary skill in the art. Such quaternary ammonium compounds are within the scope of the formulae.

Compounds of formulae herein containing an amine function may also form N-oxides. A reference herein to a compound of the formulae disclosed that contains an amine function also includes the N-oxide.

Where a compound contains several amine functions, one or more than one nitrogen atom may be oxidized to form an N-oxide. Particular examples of N-oxides are the N-oxides of a tertiary amine or a nitrogen atom of a nitrogen-containing heterocycle.

N-oxides can be formed by treatment of the corresponding amine with an oxidizing agent such as hydrogen peroxide or a per-acid (e.g. a peroxycarboxylic acid). See, e.g., Advanced Organic Chemistry, by Jerry March, 4th Edition, Wiley Interscience. More particularly, N-oxides can be made by the procedure of L. W. Deady (Syn. Comm. (1977), 7, 509-514) in which the amine compound is reacted with m-chloroperoxybenzoic acid (MCPBA), for example, in an inert solvent such as dichloromethane.

During the past 20 years, scientific and technical breakthroughs have significantly advanced RNA-based therapeutics, tremendously expanding the number of "druggable" targets. Several classes of RNA molecules, including antisense RNA, ribozymes, RNA decoys, aptamers, small interfering RNA (sRNA) and microRNA (miRNA) [6], have been investigated as potential RNA therapeutics. However, multiple challenges such as optimization of selectivity, stability, long-term safety, targeting (off-site effects) and the difficulty of delivery have limited the potential applications of RNA as a drug. The only approved antisense RNA drug to date is fomivirsen (Vitravene Isis Pharmaceuticals/Novartis) for the treatment of cytomegalovirus retinitis. The only marketed aptamer is pegaptanib (Macugen: OSI Phamaceuticals/Pfizer) for wet age-related macular degeneration (AMD).

Despite a number of limitations to RNA molecules as drugs, RNA presents an excellent target for therapeutic intervention because of its chemistries and individual conformations. RNA folds into complex combinations of three-dimensional structures comprising loops, bulges, pseudoknots and turns. The intricate architectures that RNA molecules can adopt lead to the formation of unique pockets and cavities where shape-specific rather than sequence-specific binding could be achieved [7]. In this respect, RNA conformation more closely resembles that of a protein than DNA. Whereas the standard approaches of designing drugs to target proteins have benefited from crystal structures of complexes for the last twenty years, the first crystal structures of small molecules bound to RNA pockets were solved only recently. The crystal structure of ribosomal subunits from various organisms bound to antibiotics used for decades revealed that most of the drugs bind to defined RNA motifs instead of ribosomal proteins [8-12], giving a strong impetus to the antibiotic research field (FIG. 1). Structurally, the antibiotics target different regions of the RNA molecules in the ribosome. They bind in the shallow groove (spectinomycin) [9] or the deep groove (hygromycin B) of a helix [8], at a three-adenine bulge (aminoglycosides, e.g. streptomycin, paromomycin) [9], or in the exit tunnel of the nascent polypeptide chain (macrolides) [10, 12]. The antibiotics can mimic base stacking (pactamycin) [8] or form pseudo base-pairing interactions with ribosomal bases (blasticidin S. and related aminoglycosides) [9]. Many other RNA molecules including, HIV TAR RNA [14], RNase P [15], group I introns [16] and tmRNA [17], have been proposed and evaluated to be potential targets for known antibiotics like aminoglycosides. It is clear that the current paradigm of antibiotic rational design is now shifting from targeting proteins to RNAs.

Among identified RNA targets, the riboswitch motif has attracted increasing attention. The riboswitch is a 5'-untranslated region (5'UTR) of a messenger RNA (mRNA) with a binding site for a ligand specific to that message. Binding of the ligand controls expression of the protein encoded by that mRNA via regulating transcription or translation. A riboswitch undergoes dynamic exchange between alternative conformations, each of which leads to a different biological result. Depending on the mRNA and its genetic regulation, the ligand can be a positive or negative effector of protein synthesis. A number of genes crucial to metabolite biosynthesis or transport are regulated in bacteria through the binding of the cognate metabolites to classes of mRNA riboswitches [18-20]. Riboswitches are fundamentally alternative RNA drug targets because they have evolved over millions of years as structured receptors for the purpose of binding ligands. As a consequence, riboswitches form ligand-receptor interfaces with a level of structural complexity and selectivity that approaches that of proteins. In some bacterial pathogens, the downstream genes regulated by a riboswitch are essential for bacterial survival and virulence. Therefore, designing small molecules targeting this kind of riboswitch may yield a lethal effect to bacteria pathogens.

Crystal structures of riboswitch-ligand complexes have revealed that the ligand is almost completely enveloped in the complex. The intimacy of this interaction enables the riboswitch to discriminate against even closely related analogs [21-23], thereby making the chemical and physical space highly druggable. Combined experimental data [24, 25] have provided compelling evidence that riboswitches form structured receptors that are among the most selective of any RNA targets. Thus, the riboswitch presents an opportunistic site for the design of compounds that are both highly selective and do not bind to other cellular targets. The potential toxicity of riboswitch-targeted antibiotics in humans is a major concern in this drug design strategy. If the human host carries the same riboswitch, compounds would affect the host in the same manner as the pathogenic bacteria. Importantly, several riboswitches are unique to bacterial pathogens, and not found in humans [26]. Similar to antibiotic resistance for protein-based targets, bacteria may also evolve resistance to riboswitch-targeting drugs through a mutation that disrupts binding to the riboswitch receptor. However, it may be difficult for a pathogen to evolve selective resistance to riboswitch-targeting antibiotics via a point mutation in the riboswitch. The reasons are: (1) point mutations in riboswitches would also disrupt the native metabolite ligand binding, resulting in deregulation of the associated biosynthetic pathways; and (2) when several riboswitches of the same class are targeted by a single compound, mutations in each riboswitch would be necessary to produce resistance.

Figure 2:
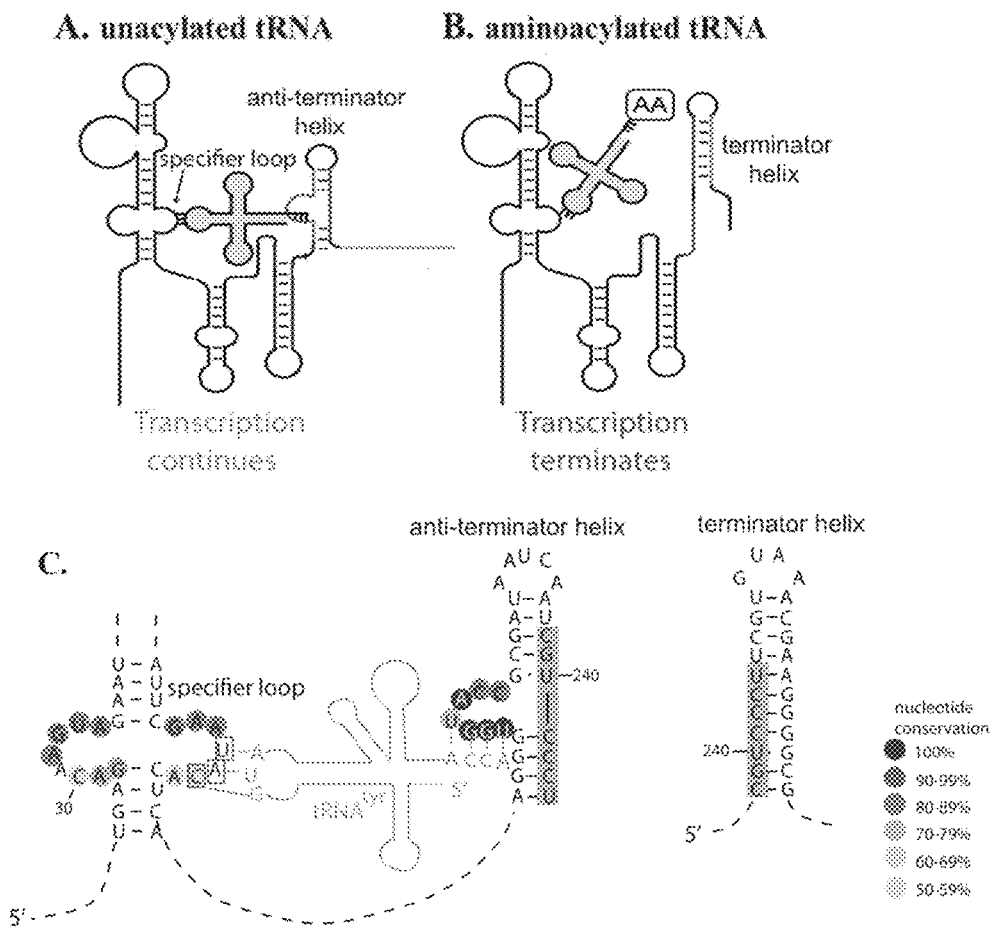
FIG. 2 shows tRNA-dependent riboswitch of aaRS gene expression unique to Gram-positive bacteria. A. Unacylated tRNA stabilizes the anti-terminator helix conformation and transcription continues. B. Aminoacylated tRNA promotes the terminator helix formation and transcription terminates prematurely. C. The proposed interaction interfaces between *B. subtilis* TyrRS leader RNA and unacylated tRNAtyr. The competing terminator and anti-terminator secondary structures are shown with the common sequence highlighted in blue. Nucleotide conservation in all 722 T-box sequences analyzed was color coded accordingly. Adapted from Henkin [31], Gerdeman et al. [36] and Gutierrez-Preciado, et al.[29].

Maintenance of appropriate pools of aminoacylated tRNAs for protein synthesis is essential for bacterial viability. This requires not only balanced levels of tRNAs, but also their cognate aminoacyl-tRNA synthetases (aaRSs) that catalyze the tRNA aminoacylation. In Gram-positive bacteria, including MRSA, transcription of most aaRS genes is uniquely regulated by the specific tRNA substrate binding to the 5'UTR of the nascent mRNA. Though the size of tRNA as a regulatory ligand contrasts greatly with the more common small metabolite-regulated riboswitches, the tRNA-dependent riboswitch operates similarly in that the completion of transcription is controlled through a resulting conformational change (FIGS. 2A,B). Similar to other T-box family genes, the 5'UTR of the mRNA of the regulated aaRS gene exhibits a conservation of sequence and structural features [27-31] (FIG. 2C). Segments of 5'UTR RNA can fold to form two alternative hairpin structures, an intrinsic transcription terminator or a competing transcription anti-terminator (FIG. 2). Formation of the terminator hairpin prematurely terminates transcription.

Figure 3:
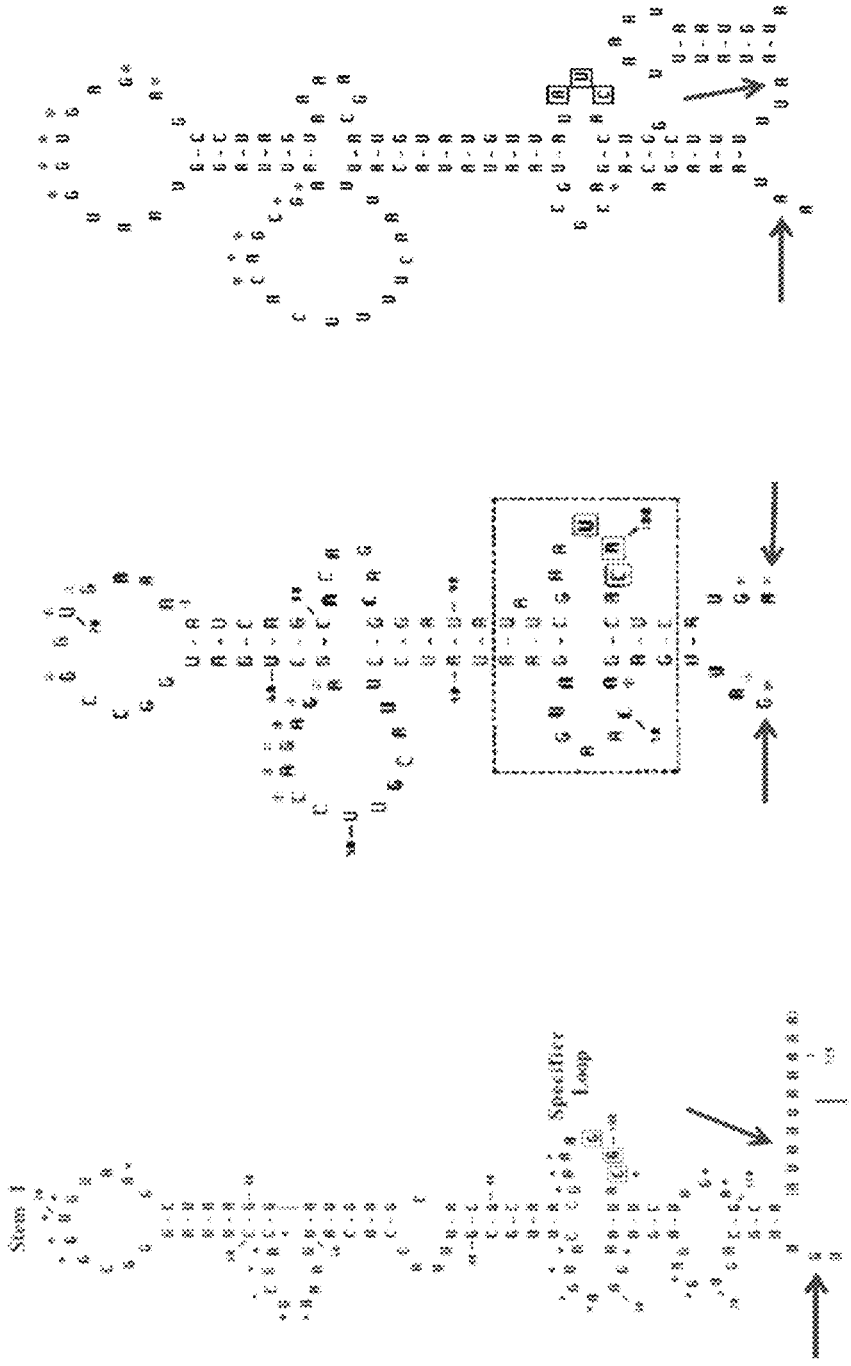
FIG. 3 shows three specifier hairpin RNAs from Gram-positive bacteria that may be useful in identifying potential Gram-positive specific anti-bacterial agents.

The unacylated tRNA is the key positive effector of this regulatory riboswitch in its binding to the 5'UTR of the nascent mRNA, stabilizing the anti-terminator conformation, and leading to transcription of the downstream aaRS gene (FIG. 2A). The specificity of this 5'UTR:tRNA interaction is determined, at least in part, by pairing of the tRNA's specific anticodon with a complimentary codon sequence in the specifier loop (FIG. 2C, residues in red boxes), whereas stabilization of the anti-terminator is dependent on base-pairing of the universal tRNA terminal (5'-NCCA-3') with complementary residues (5'-UGGN-3') in a 7-nt bulge of the anti-terminator [32, 33] (FIG. 3C). In response to a decreased pool of aminoacylated tRNA, unacylated tRNA recognized by the nascent transcript results in increased expression of aaRS genes, which continue to aminoacylate more tRNAs. The covalently bound amino acid of an aminoacylated tRNA negates tRNA binding to the nacent mRNA and thus, an intrinsic terminator helix is formed and transcription is relinquished prior to the coding sequence of the mRNA (FIG. 3B).

Figure 4:
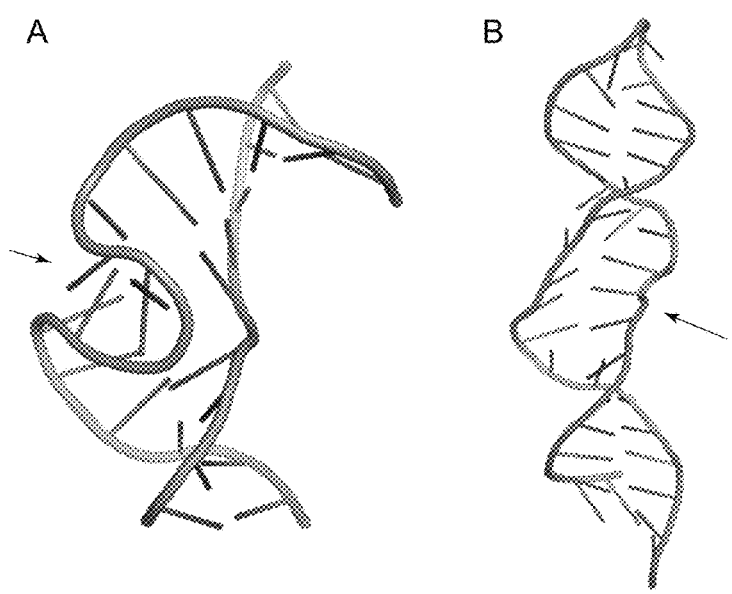
FIG. 4 shows the NMR structures of anti-terminator (A) and specifier loop (B) of the tRNA dependent T-box riboswitch. The anti-terminator 7-nt bulge and the codon sequence are pointed by arrows. Adapted from Gerdeman et al. [34] and Wang and Nikonowicz [35].
Figure 5A:
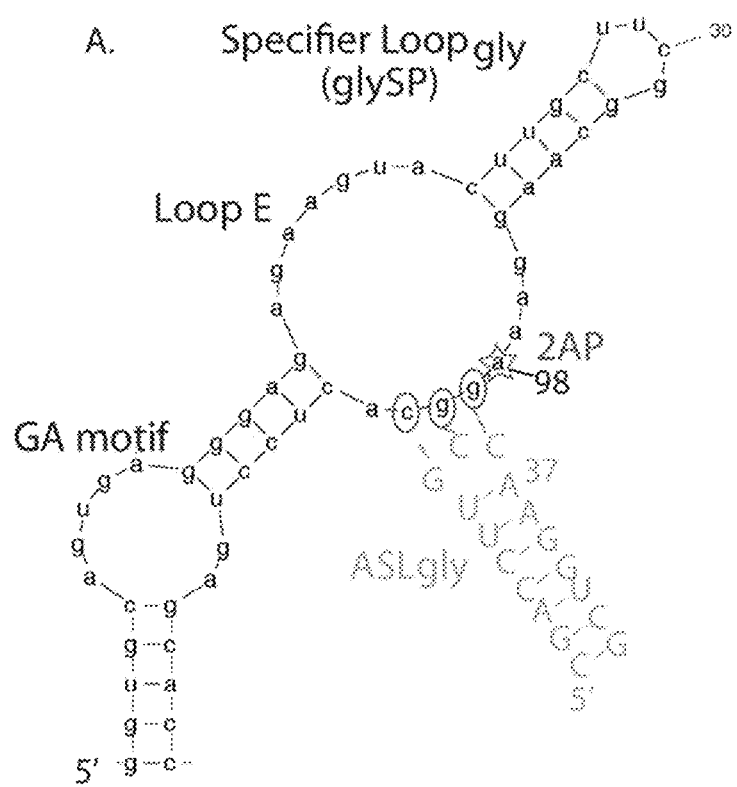
FIG. 5 show sequence and proposed interaction of truncated 56-nt specifier loop (glySP) and 17-nt ASLgly (A). The specifier sequence GGC is highlighted by blue ovals. 2-amino purine (2AP) was introduced to position 98 (shown in red star) to monitor the fluorescence change upon ASL binding. (B.) Dramatic fluorescence increase at 375 nm was observed upon titrating ASLgly to 1 µM 2AP98-glySP solution (Lu, Agris, unpublished data). (C.) Binding of $^{32}$P-tRNA$^{Gly}$ by the 5'UTR (183) monitored by spin-column capture and scintillation counting. (D.) Binding of tRNA$^{Gly}$ by the 5'UTR (183) monitored by ITC. Two transitions were observed. (E.) Binding of a 'hit' to the glyRS mRNA Specifier Loop-2AP98. Fluorescence: Gray-Specifier Loop-2AP98; Red-plus compound, 1:100. Of 20 compounds, 5 induced a dramatic fluorescence decrease indicative of the binding and a possible change in RNA conformation.
Figure 5B:
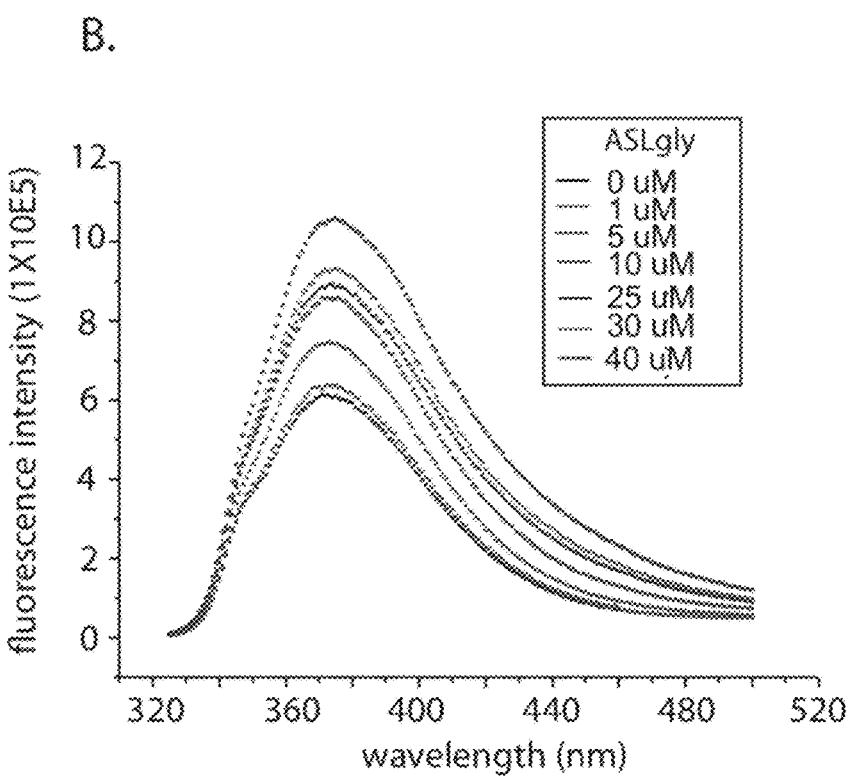
Figure 5C:
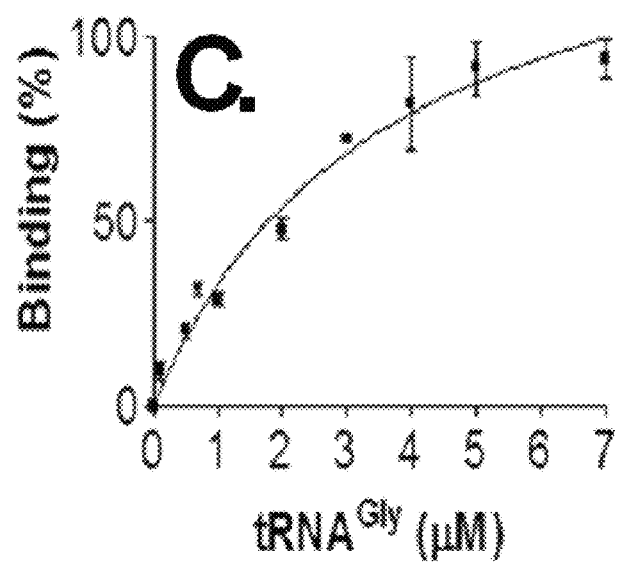
Figure 5D:
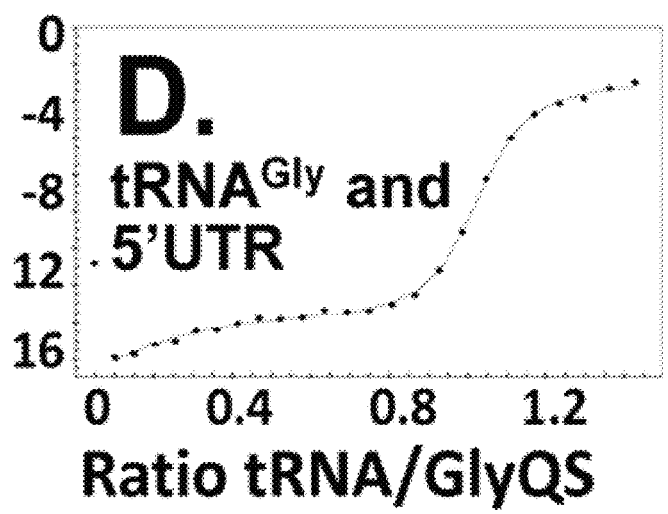
Figure 5E:
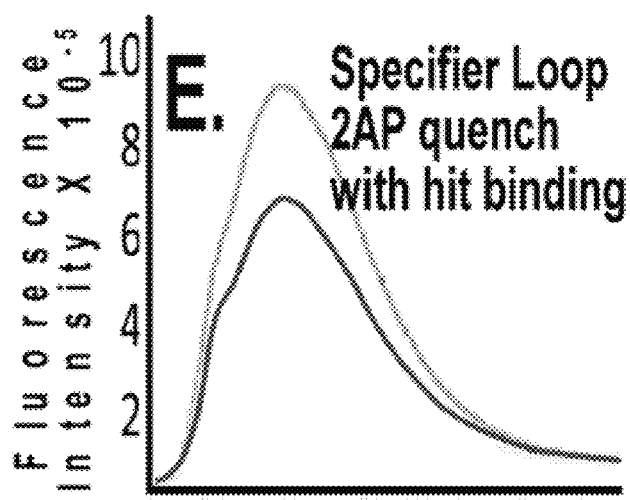
Figure 6:
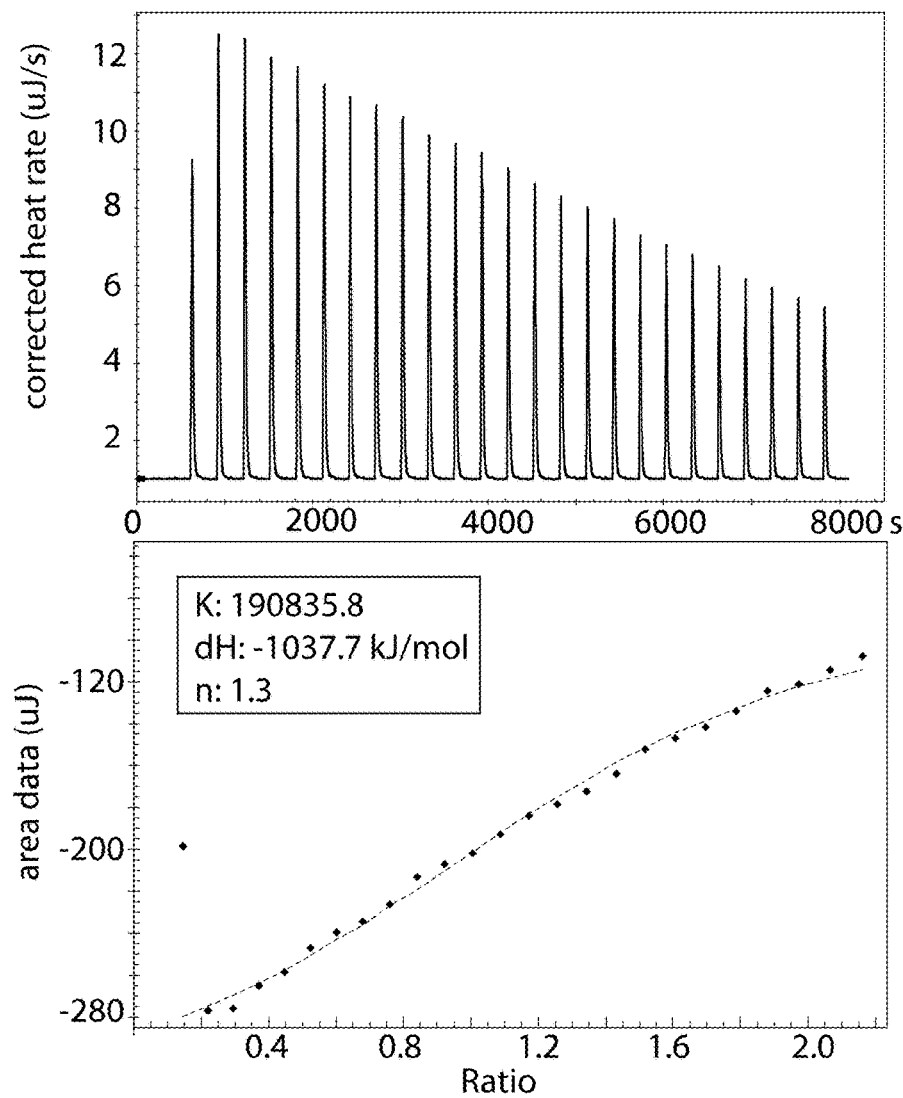
FIG. 6 shows the ITC profile for the binding of 130 µM ASLgly with 20 µM GlyQS T-box specifier loop (glySP) at 25° C. It indicates a weak exothermic binding event. Non-linear least squares fit using "one-site binding" model is shown in black dashed line.

Until recently, no structural information was available for the T-box riboswitch. The anti-terminator and specifier loop helix structures were solved recently by the Hines [34] and Nikonowicz [35] groups, respectively, using Nuclear Magnetic Resonance (NMR) (FIG. 4). In the anti-terminator structure (FIG. 4A), the 7-nucleotide bulge region that ultimately interacts with the acceptor end of tRNA exhibits extensive stacking (encompassing the highly conserved 3'-ACC residues (FIG. 2C). However, the UGGA 5'-end of the bulge exhibits great conformational flexibility and does not show any evidence of pre-organizing for binding to tRNA. This level of flexibility has been reported to be important for anti-terminator function. Introduction of a substitution at one of the conserved C residues results in a substantial increase in bulge flexibility and a corresponding decrease in tRNA binding activity in vitro, and tRNA-dependent anti-termination in vitro and in vivo [34, 36]. This structural flexibility makes the anti-terminator a very poor drug target. Moreover, the nucleotide bases in tRNA interacting with the anti-terminator are non-specific; they are located in a universal tRNA terminus (5'-NCCA-3') that is found throughout all domains of life, including humans.

In contrast, appropriately named specifier loop domain is located in the Stem I of the 5'UTR and contains nucleotides that are complementary to and pair with the tRNA anticodon. Stem I has two major common RNA structural motifs (loop E and K-turn motifs) and both are crucial for proper transcriptional regulation [37, 38]. The loop E motif in the specifier loop provides a stable platform that appears to help position the specifier nucleotides to accept the anticodon of the cognate tRNA. This motif is similar to that found in several prokaryotic and eukaryotic rRNAs and the hairpin ribozyme [39, 40]. The NMR-derived structure (FIG. 4B) of a model Stem I in the 5'UTR of the tyrosyl-tRNA synthetase (TyrRS) mRNA supports the presence of the Loop E motif in the specifier loop. The single-strand specifier nucleotides stack with their Watson-Crick edges displaced toward the minor groove [35]. The K-turn, or GA, sequence motif is joined to the specifier loop domain by a 3- to 5-bp helix. The NMR structure showed the K-turn sequence motif has several noncanonical base pairs typical of K-turn structures, but adopts an extended conformation (FIG. 4B). These motifs create an intricate folding pocket in the specifier loop, which offer a unique drug target. In fact, a recently completed study of in silico docking simulations of 25,000 drug-like compounds on the Stem I structure (Cantara and Agris, unpublished data) indicated that 20 compounds bind to the specifier loop with specificity and selectivity. The overall structure of the specifier loop is well ordered, with only a few nucleotides exhibiting a moderate degree of mobility. The specifier nucleotide bases are stacked, but their Watson-Crick edges are not uniformly displayed. The 3'-two bases are rotated toward the minor groove and readily accessible to the tRNA anticodon, whereas the 5'-base is rotated toward the major groove with its base pairing edges pointing toward the helix axis.

As the specific recognition of the cognate unacylated tRNA can occur in the absence of any other cellular factors for the glycyl-tRNA synthetase (GlyQS) 5'UTR [27], determining the structure of the specifier loop of the GlyQS riboswitch in the complex with tRNA will provide more relevant and accurate structural information for the proposed novel therapeutic drug target. Disrupting the tRNA:5'UTR interaction by targeting the mRNA with a small molecule would result in the riboswitch conformation in the OFF position. Small molecule intervention would negate transcription of the downstream aaRS gene, and aaRS proteins critical to the pathogen's viability would not be synthesized, preventing further infection.

Without wishing to be bound by theory, the binding of small compounds to the glySP is thought to deform the specifier loop and thus, inhibit the interaction of the nascent transcript with the tRNA. Transcription of the aaRS gene is then terminated.

In order to understand the chemical and physical space of the specifier loop as a possible validated target of drug intervention, a small set of compounds was identified. The compounds of the invention, subgroups and examples thereof, are believed to perturb the interaction of the specifier loop and tRNA anticodon stem and loop of a T-box riboswitch unique to Gram-positive bacteria and therefore, may be useful in the treatment of infection caused by Gram-positive bacteria.

Identification of Small Molecules

Within a collaborative research program with Albany Molecular Research, Inc. (Albany, N.Y.), 200 high affinity small compounds likely to disrupt tRNA's binding of the Specifier Loop codon were selected from screening a library of 280,000 diverse compounds. Using the NMR-derived solution structure of a Specifier Loop from a truncated construct of the tyrRS mRNA 5'UTR41 and in an iterative manner the Glide in silico docking program (Schrodinger, Inc.), we have identified high-scoring compounds most likely to interact with the Specifier Loop. Most of the compounds identified have a flat "pi" stacking portion with a tether to an aliphatic basic amine group. Additionally, most compounds were ionized with two protonated groups when docked. Additional docking simulations led to 28 putative, high affinity compounds from this list.

Twenty of these bound specifically to a cleft within the tyrRS Specifier Loop structure and not to the codon. The cleft appears to be the result of the conserved adenosine stacking interactions (FIG. 7A).[72, 73] These compounds appear to also have in common a core chemistry. None of the compounds identified are within the family of a current antibiotic such as aminoglycosides, compounds known to be good binders of RNA, but that prove difficult to alter in their toxicity to humans.

Figure 7:
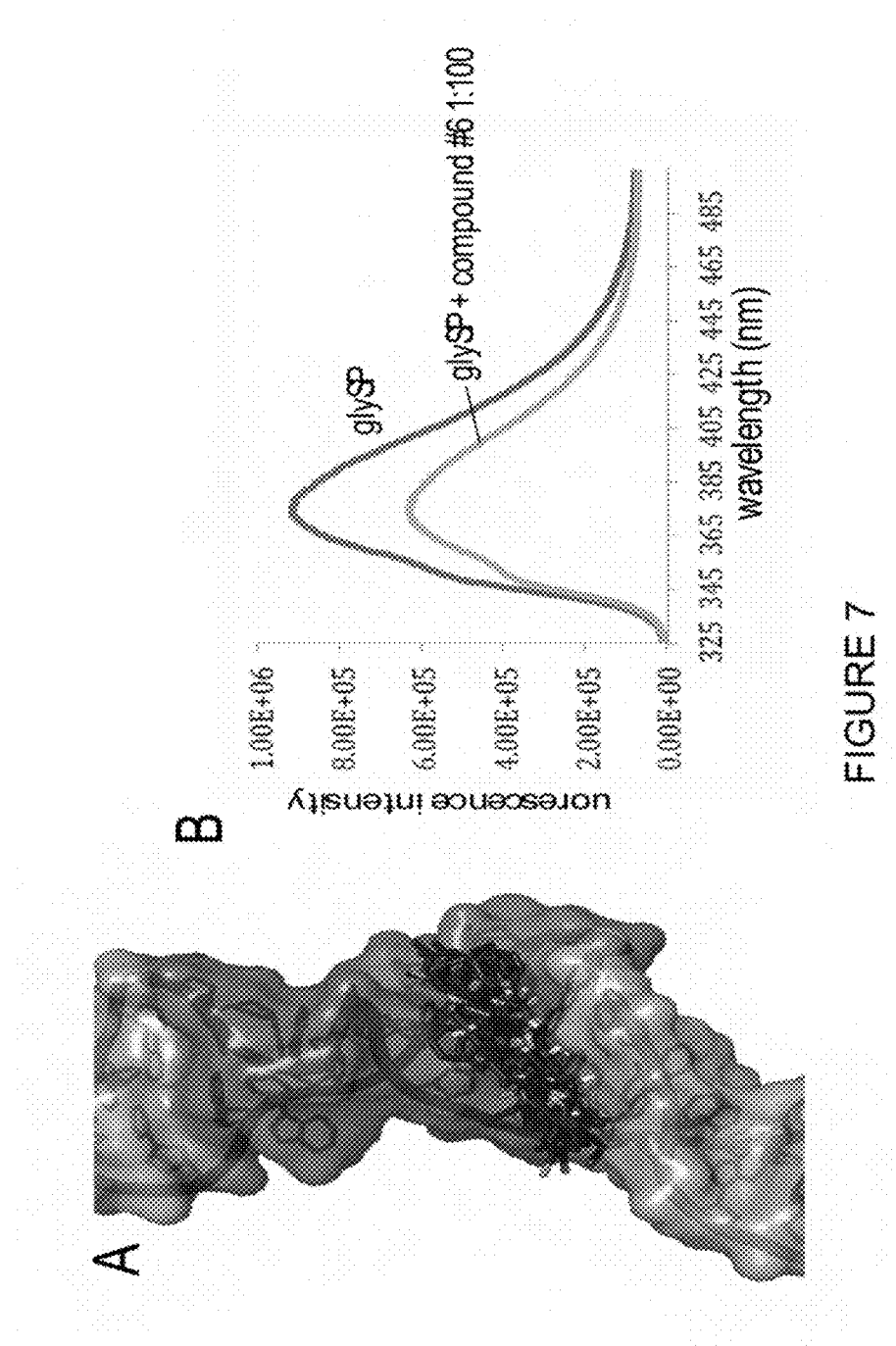
FIG. 7 In silico modeling identified 20 compounds that bound to the same cleft of the TyrRS mRNA specifier loop. A. Superposition of all 20 compounds bound to the specifer loop. B. Preliminary fluorescence assay of compounds binding to the r2AP98-glySP. 5 out of 20 compounds induced a dramatic fluorescence decrease at 375 nm indicative of the binding of the small molecules and a possible conformational change in the RNA.
Figure 8:
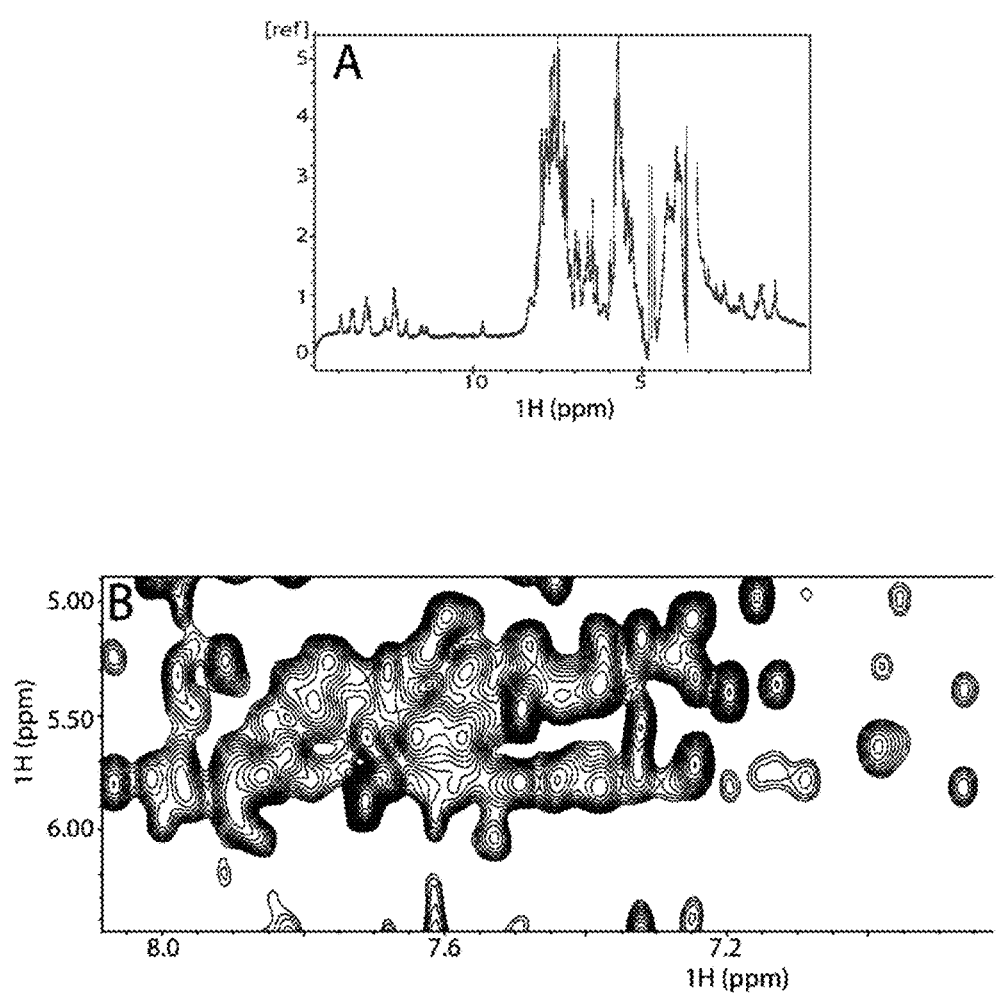
FIG. 8 Preliminary NMR studies of the glySP. A. One dimensional imino spectrum of glySP (20° C.). The 1H NMR spectrum of the exchangeable imino protons indicate stable hydrogen bonding for the three Watson-Crick based paired helixes. B. Two dimensional wg-NOESY spectrum of glySP (20° C.). The base-H1' region showed that the peaks are sharp and well-resolved despite the size of the RNA and the lack of stable isotope editing.
Figure 9:
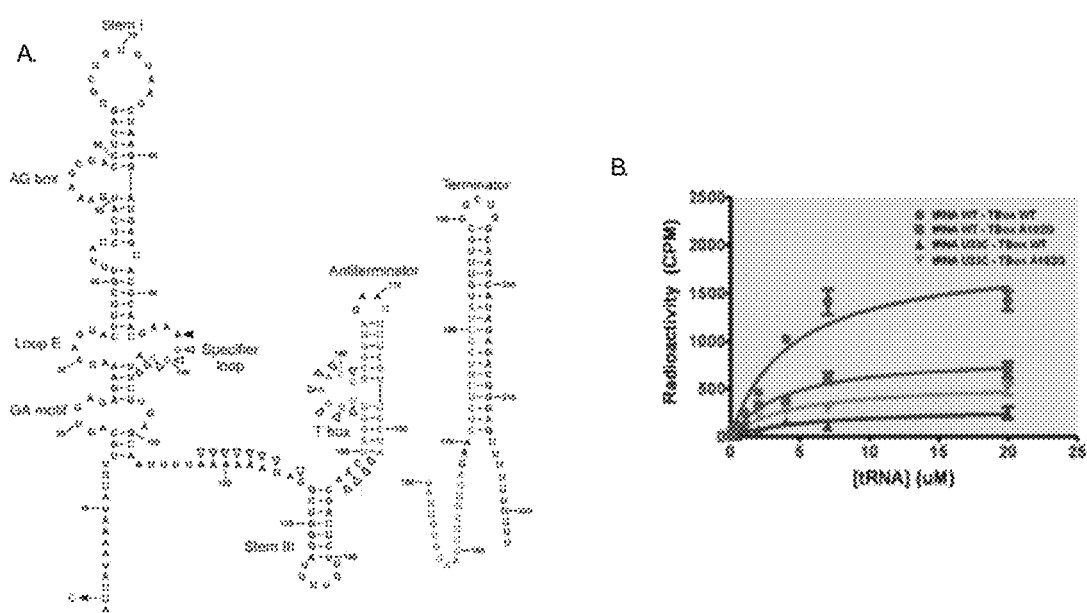
FIG. 9 A. *Bacillus subtilis* GlyQS leader RNA secondary structure. The 182-nt 5'UTR (5'UTR-anti), designed to lack a conformational change of terminator to anti-terminator upon binding of unacylated tRNA, ends right after the anti-terminator helix, adapted from Yousef, et al. [42]. B. Spin column binding assay of the 5'UTR-anti titrated with 32P-end labeled tRNAgly. Mutations A102G in the 5'UTR and U33C in tRNAgly both dramatically weakened binding of tRNA to 5'UTR.
Figure 10:
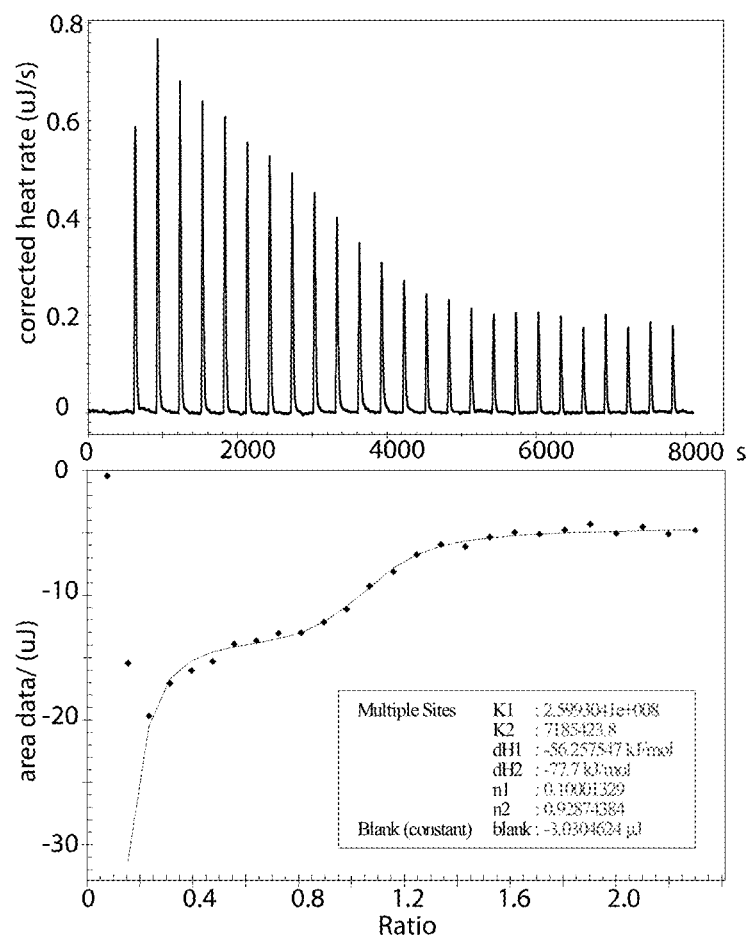
FIG. 10 Top. ITC profile for the binding of tRNAgly (60 µM) to 5'UTR (9 µM; 25° C.). A two component exothermic binding is observed. Bottom. Non-linear least squares fit using "one-site binding" model for the second exothermic event (black line).

The 20 top binders predicted to interact with the cleft of the tyrRS mRNA Specifier Loop were characterized using the Specifier Loop-2AP98 fluorescence assay. Three compounds having very low solubility in water and four compounds inherently fluorescent in the same range as 2AP could not be assessed. Of the remaining 13 compounds, five exhibited a dramatic fluorescence quenching when they were mixed with the Specifier Loop-2AP98 at a 100:1 ratio (FIG. 7B). This indicated probable binding to the Specifier Loop and induction of a conformational change at position 2AP98, adjacent to the codon sequence.

The same 20 top binders and 8 additional predicted to interact with the cleft of the tyrRS mRNA Specifier Loop were selected from subsequent docking and preliminary fluorescence data. All 28 compounds were tested for their ability to inhibit the growth of *B. subtilis* using a standard disc diffusion assay.[42] Four of the 28 compounds displayed significant clearing around the disc, indicating possible antibacterial activity. The results are shown in Table 1.

TABLE 1

| Compound | Disk diffusion assay result | |
|---|---|---|
| | ZOI observed | ZOI NOT observed |
| 1 | | ✓ |
| 2 | | ✓ |
| 3 | | ✓ |

TABLE 1-continued

| Compound | Disk diffusion assay result | |
|---|---|---|
| | ZOI observed | ZOI NOT observed |
| 4 | | ✓ |
| 5 | | ✓ |
| 6 | ✓ | |
| 7 | ✓ | |
| 8 | | ✓ |
| 9 | | ✓ |
| 10 | | ✓ |
| 11 | | ✓ |
| 12 | | ✓ |
| 13 | | ✓ |
| 14 | | ✓ |
| 15 | | ✓ |
| 16 | | ✓ |
| 17 | | ✓ |
| 18 | ✓ | |
| 19 | | ✓ |
| 20 | | ✓ |
| 21 | | ✓ |
| 22 | | ✓ |
| 23 | | ✓ |
| 24 | ✓ | |
| 25 | | ✓ |
| 26 | | ✓ |
| 27 | | ✓ |
| 28 | | ✓ |

ZOI = zone of inhibition

Two compounds (PKZ 6 & 18) selected from in silico screens and antibacterial assays inhibited growth of *B. subtilis, B. cereus, S. pneumoniae*, and *S. aureus* at moderate concentrations. The identity and purity of both PKZ 6 and 18 was confirmed by mass spectroscopy. Forty commercially available compounds chosen on the basis of initial in silico selections and similarity to our two hits were screened by disc diffusion assay (DDA) to determine their relative antibacterial activity with *S. aureus*. These DDAs revealed six PKZ18 analogs and eight PKZ6 analogs with antibacterial activity against *S. aureus*. These 14 compounds were further evaluated by minimum inhibitory concentration assays (MIC)[41,42], and minimum bactericidal assays (MBC)[41] to confirm antibacterial activity, determine the concentration at which *S. aureus* growth is inhibited in liquid culture (MIC) and if they are acting as bacteriostatic or bactericidal agents (MBC). MIC assays were also conducted with *E. coli* as an indication of compound specificity since *E. coli* does not contain Tbox regulatory mechanisms. The current results are shown in Tables 3 through 5 below. Representative embodiments are shown below.

| Compound No. | Structure |
|---|---|
| PKZ0603 | 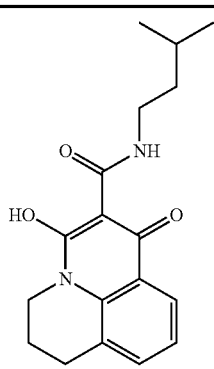 |
| PKZ0605 | 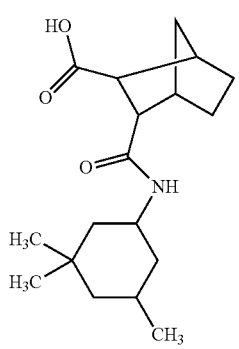 [SMILES: CC1CC(NC(=O)C2C3CCC(C3)C2C(=O)O)CC(C)(C)C1] |
| PKZ0607 | 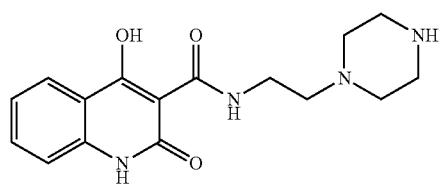 [SMILES: O=C(NCCN1CCNCC1)c1c(O)c2ccccc2[nH]c1=O] |
| PKZ0609 | 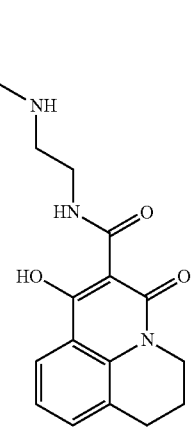 |
| PKZ0610 | 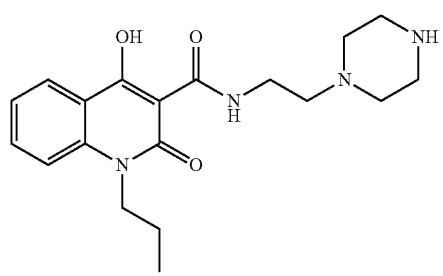 [SMILES: CCCn1c(=O)c(C(=O)NCCN2CCNCC2)c(O)c2ccccc21] |

-continued

| Compound No. | Structure |
|---|---|
| PKZ0611 | 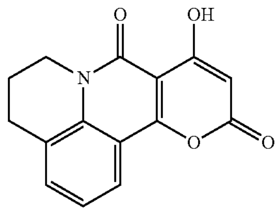 [SMILES: O=c1cc(O)c2c(=O)n3c4c(cccc4c2o1)CCC3] |
| PKZ0613 | 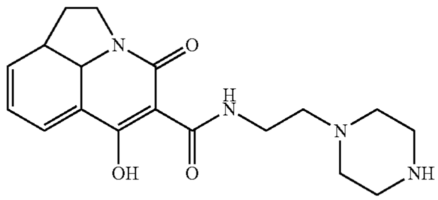 [SMILES: O=C(NCCN1CCNCC1)C1=C(O)C2=CC=CC3CCN(C1=O)C23] |
| PKZ0615 | 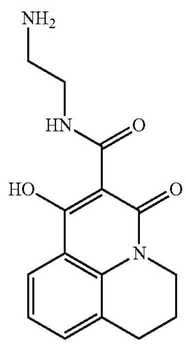 [SMILES: NCCNC(=O)c1c(O)c2cccc3c2n(c1=O)CCC3] |
| PKZ6 | 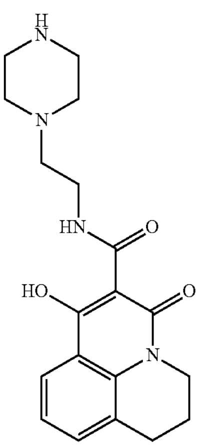 [SMILES: O=C(NCCN1CCNCC1)c1c(O)c2cccc3c2n(c1=O)CCC3] |
| PKZ18 | 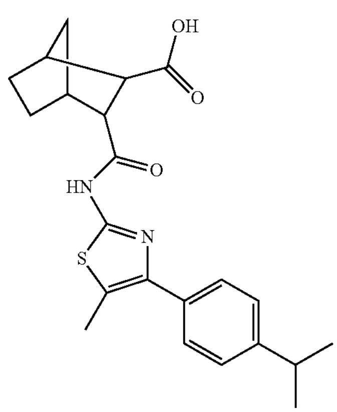 [SMILES: Cc1sc(NC(=O)C2C3CCC(C3)C2C(=O)O)nc1-c1ccc(C(C)C)cc1] |

-continued
| Compound No. | Structure |
|---|---|
| PKZ1805 | 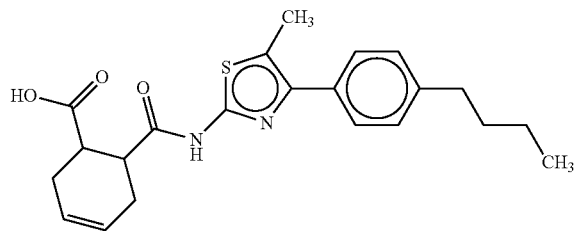 |
| PKZ1808 | 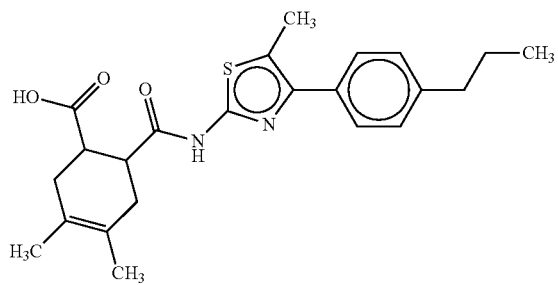 |
| PKZ1810 | 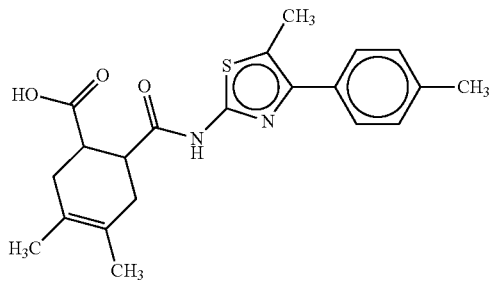 |
| PKZ1819 | 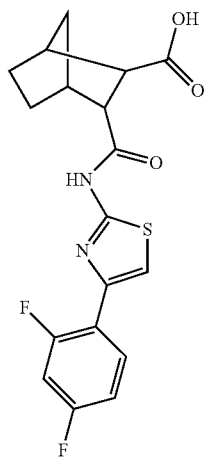 [SMILES: O=C(O)C1C2CCC(C2)C1C(=O)Nc1nc(-c2ccc(F)cc2F)cs1] |

-continued

| Compound No. | Structure |
|---|---|
| PKZ1820 | 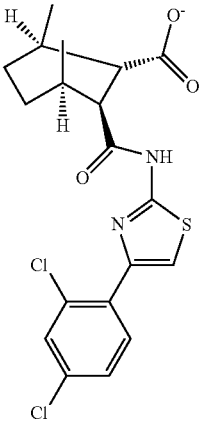 |
| PKZ1813 | 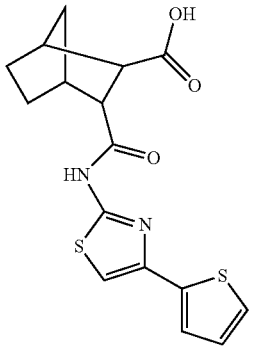 [SMILES: O=C(O)C1C2CCC(C2)C1C(=O)Nc1nc(-c2cccs2)cs1] |
| PKZ7 | 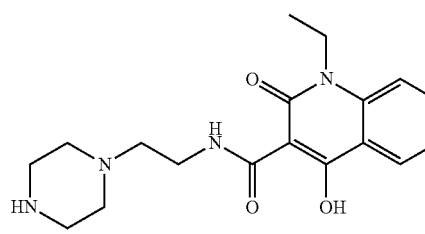 |

Broth microdilution assays[77, 78] were performed with *B. subtilis*, and *S. aureus* to determine the lowest compound concentration inhibiting visible growth, i.e., minimum inhibitory concentration (MIC) of the 4 original compounds. *E. coli* served as negative control as Gram negative bacteria do not have tRNA-dependent riboswitches. The results are shown in Table 2. MIC data revealed that 3 of the 4 compounds (6, 7 and 18) demonstrating activity in the disc diffusion assay were active against *B. subtilis*. The insolubility of the fourth compound may account for its lack of antibacterial activity. Two of the four compounds, 6 and 18 also displayed antibacterial properties against *S. aureus*. The MICs of each compound are moderate. Compound 18 did not inhibit growth of *E. coli*. Compounds 6 and 7 displayed moderate antibacterial activity against *E. coli*, indicating that there may be alternate or multiple targets for these two compounds.

TABLE 2

| Bacteria | MIC (MBC) values (µg/mL) | | | |
|---|---|---|---|---|
| | 6 | 7 | 18 | Gentamicin |
| *B. subtilis* BGSC 1A1 | 32 (IND) | 32 (IND) | 64 (64) | 0.125 (0.25) |
| *B. cereus* ATCC 7064 | 128 (256) | 512 (N/O) | 64 (64) | 1 (2) |
| *S. aureus* ATCC 29213 | 256 (N/O) | N/O (N/D) | 64 (N/O) | 0.5 (8) |
| *S. pneumoniae* ATCC 49619 | 64 (N/D) | 128 (N/D) | 64 (N/D) | 4 (N/D) |
| *E. faecalis* ATCC 29212 | 128 (N/O) | 512 (N/O) | N/O (N/O) | 8 (32) |
| *E. coli* ATCC 25922 | 256 (256) | 512 (512) | N/O (N/D) | 1 (1) |
| *P. aeruginosa* ATCC 27853 | N/O (N/D) | N/O (N/D) | N/O (N/D) | 1 (4) |

MIC = Minimum inhibitory concentration;
MBC = minimum bactericidal concentration;
IND = indeterminate;
N/O = not observed;
N/D = not determined For three of the compounds initially identified, PKZ06, PKZ07 and PKZ18, the following table shows the toxicity of the compounds on a monolayer of Human Embryonic Kidney (HEK293) cells.

TABLE 3

|  | 16 hr post exposure Morphology | 16 hr post exposure % Live | 24 hr post exposure Morphology | 24 hr post exposure % Live | 24 hr post exposure % Confluent |
|---|---|---|---|---|---|
| Conc. PKZ06 |  |  |  |  |  |
| 128 ug/ml | Rounded and Detached | 0 | Rounded and Detached | 0 | 0 |
| 64 ug/ml | Mix of Normal and Detached | 60 | Mix of Normal and Detached | 25 | 15 |
| 32 ug/ml | Normal | 100 |  | 70 | 50 |
| 0 ug/ml | Normal | 100 | Normal | 100 | 90 |
| Conc. PKZ07 |  |  |  |  |  |
| 128 ug/ml | Rounded and Detached | 0 | Rounded and Detached | 0 | 0 |
| 64 ug/ml | Mix of Normal and Detached | 80 | Mix of Normal and Detached | 75 | 80 |
| 32 ug/ml | Normal | 100 | Normal | 90 | 90 |
| 0 ug/ml | Normal | 100 | Normal | 100 | 90 |
| Gent 1 ug/ml | Normal | 100 | Normal | 100 | 90 |
| Conc. PKZ18 |  |  |  |  |  |
| 128 ug/ml | Normal | 100 | Rounded and Detached | 15 | 15 |
| 64 ug/ml | Normal | 100 | Mix of Normal and Detached | 90 | 90 |
| 32 ug/ml | Normal | 100 | Normal | 100 | 90 |
| 0 ug/ml | Normal | 100 | Normal | 100 | 90 |
| Gent 1 ug/ml | Normal | 100 | Normal | 100 | 90 |

Table 4 shows the results of the disc diffusion assay conducted with PKZ6 and 18 analogs (see chart above). All compounds were tested at a concentration of 150 µg/ml.

TABLE 4

Analog Disk diffusion Assay Results

| Compound | ZOI observed | ZOI NOT observed |
|---|---|---|
| 1801 |  | ✓ |
| 1802 |  | ✓ |
| 1803 |  | ✓ |
| 1804 |  | ✓ |
| 1805 | ✓ |  |
| 1806 |  | ✓ |
| 1807 |  | ✓ |
| 1808 | ✓ |  |
| 1809 |  | ✓ |
| 1810 | ✓ |  |
| 1811 |  | ✓ |
| 1812 |  | ✓ |
| 1813 | ✓ |  |
| 1814 |  | ✓ |
| 1815 |  | ✓ |
| 1816 |  | ✓ |
| 1817 |  | ✓ |
| 1818 |  | ✓ |
| 1819 | ✓ |  |
| 1820 | ✓ |  |
| 0601 |  | ✓ |
| 0602 |  | ✓ |
| 0603 | ✓ |  |
| 0604 |  | ✓ |
| 0605 | ✓ |  |
| 0606 |  | ✓ |
| 0607 | ✓ |  |
| 0608 |  | ✓ |
| 0609 | ✓ |  |
| 0610 | ✓ |  |
| 0611 | ✓ |  |
| 0612 |  | ✓ |

TABLE 4-continued

Analog Disk diffusion Assay Results

| Compound | ZOI observed | ZOI NOT observed |
|---|---|---|
| 0613 | ✓ |  |
| 0614 |  | ✓ |
| 0615 | ✓ |  |

ZOI = zone of inhibition

Table 5 shows antibacterial activity of hit compound analogs. Values represent triplicate experiments. Minimum bacterial concentration (MIC) and minimum bactericidal concentration (MBC) were evaluated for each compound.

TABLE 5

Analog MIC and MBC Results (µg/mL)

| Compound | S. aureus MIC (MBC) | E. coli MIC (MBC) |
|---|---|---|
| 1805 | N/D | N/D |
| 1808 | N/D | N/D |
| 1810 | 256 (N/O) | 512 (N/O) |
| 1813 | N/O (N/O) | N/O (N/O) |
| 1819 | 128 (512) | N/D |
| 1820 | 64 (N/O) | N/D |
| 0603 | 512 (N/O) | 512 (N/O) |
| 0605 | N/D | N/D |
| 0607 | 512 (N/O) | 256 (N/O) |
| 0609 | N/D | N/D |
| 0610 | N/D | N/D |
| 0611 | N/D | N/D |
| 0613 | N/D | N/D |
| 0615 | N/D | N/D |

MIC = Minimum inhibitory concentration;
MBC = minimum bactericidal concentration;
N/O = not observed at concentrations tested (512-0.25 µg/mL;
N/D = not determined Pharmaceutical Formulations While it is possible for the active compound to be administered alone, it may be advantageous to present it as a pharmaceutical composition (e.g. formulation).

Thus, the present invention further provides pharmaceutical compositions, as defined above, and methods of making a pharmaceutical composition comprising (e.g admixing) at least one compound of formulas I and II (and sub-groups thereof as defined herein), together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavoring agents, sweeteners, taste masking agents, stabilizers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) or (II) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilization of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilizing the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilized) condition requiring only the addition of the sterile liquid carrier, for example water for injections, immediately prior to use.

The pharmaceutical formulation can be prepared by lyophilizing a compound of formula (I), or sub-groups thereof. Lyophilization refers to the procedure of freeze-drying a composition. Freeze-drying and lyophilization are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or uncoated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

Compound of formulas I and II may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13th March 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% (w/w) disintegrants, 0-5% (w/w) lubricants, 0-5% (w/w) flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) co-solvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

Compounds of formulas I or II will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound is administered to a patient in need thereof (for example a human or animal patient) in an amount sufficient to achieve the desired therapeutic effect.

Methods of Treatment

The compounds of formulas I and II and sub-groups as defined herein may be useful in the prophylaxis or treatment of infectious disease caused by Gram-positive bacteria.

The compounds are generally administered to a subject in need of such administration, for example a human or animal patient.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient is given an infusion of a compound of the formulas (1-3) for periods of one hour daily for up to ten days in particular up to five days for one week, and the treatment repeated at a desired interval such as two to four weeks, in particular every three weeks.

More particularly, a patient may be given an infusion of a compound of the formulas 1-3 for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used is commensurate with the nature of the disease or physiological condition being treated and is at the discretion of the physician.

It has been discovered that the anti-bacterial agents can be used as a single agent or in combination with other antibacterial agents. For example, it may be beneficial to combine an agent that targets the T-box riboswitch with another agent that acts via a different mechanism.

The compounds as defined herein can be administered as the sole therapeutic agent or they can be administered in combination therapy with one of more other compounds (or therapies) for treatment of a particular disease.

EXAMPLES

Compounds

PKZ-6 (BAS 03189420) and PKZ-7 (BAS 03848004) were obtained from Asinex and PKZ-18 (AK-968/41171234) was obtained from Ambinter. These compounds were dissolved in water to a final concentration of 10.24 mg/mL and aliquots of the resulting stock solutions were stored at −80° C. until use.

r2AP Fluorescence Assay

Fluorescence of the r2AP98-glySP is used to assess its binding to the ASLgly. First, the linear range of r2AP98-glySP concentration is determined for which a corresponding linear fluorescence increase is observed ($\lambda$ex=310 nm; $\lambda$em=375 nm). r2AP98-glySP at the optimized concentration is titrated with ASLgly or the control ASLphe from 0 to 100-fold excess. The binding affinity is calculated from the fitted fluorescence intensity change profile [41]. The fluorescence of the chemically synthesized ASL is analyzed to ensure no interference from the uncleaved protecting groups on ASL. Liquid handler and microtiter plate reader instruments will facilitate the assay's accuracy and efficiency.

Electrophoretic Mobility Shift Assays (EMSA)

The interaction of the glySP with the ASLgly is studied with a native EMSA, allowing a direct observation of the interaction. Different ratios of glySP:ASLgly is used to study the glySP band shift upon binding the ASLgly. The gel buffer conditions is optimized and may require magnesium ions for optimal binding [35]. Preliminary ITC data indicated that the binding affinity for the ASL is moderate (Kd~5 $\mu$M), which is understandable for a regulatory system in control of sensitive gene expression. Thus, it is possible the glySP:ASLgly complex could be disrupted by the conditions of gel electrophoresis. Low running voltage (80 V) and temperature (4° C.) may help stabilize the complex. A 32P-end labeled ASLgly titration may be required for an enhanced sensitivity to detect the shifted band with a phosphorimager. Noncognate ASLphe is used as a control as it is unable to base pair to the codon sequence of glySP.

NMR Studies

Binding of the ASLgly to the site-specific 15N labeled glySP is studied with NMR (1 D imino proton and 2D heteronuclear multiple quantum coherence, HMQC). Only the 15N labeled nucleotide of the glySP is observed, greatly simplifying the spectrum and enabling direct observation of the H-bond formation between codon and anticodon. The observed NMR signal pattern will disclose the exchange rate of free glySP vs. bound glySP. Temperature-dependent NMR experiments are conducted to obtain the "melting" temperature of the interaction. The small molecule selected from our prior in silico modeling that best binds the glySP is titrated into the complex to determine its ability to break the codon-anticodon H-bonding.

Determination of MIC Values

Strains were grown on trypticase soy agar (TSA) with 5% sheep blood at 37° C. for 24 hours. Five isolated colonies were used to inoculate 5 mL cation-adjusted Mueller-Hinton broth (CAMHB) contained in a 50 mL centrifuge tube. The resulting culture was incubated shaking at 200 rpm for 3 hours at 37° C. and then diluted in CAMHB until its turbidity matched that of a 0.5 McFarland standard (OD625 0.08-0.10). After the culture had been standardized against a 0.5 McFarland standard, it was diluted 1:10 in CAMHB and then 5 $\mu$L of this dilution was added to the appropriate wells of a 96-well, flat-bottomed tissue culture plate in which each row contained a twofold dilution series of a particular compound ranging in concentration from 0.25 $\mu$g/mL to 512 $\mu$g/mL. Each plate also included a sterility control well containing CAMHB to which standardized inoculum was not added and a growth control well containing CAMHB to which 5 $\mu$L standardized inoculum was added. A twofold gentamicin dilution series ranging in concentration from 0.0625 $\mu$g/mL to 128 $\mu$g/mL was also included on each plate. With the exception of the sterility control well, all wells were inoculated within 15 minutes of inoculum preparation to ensure that the starting concentration of bacteria in each well was approximately $5 \times 10^5$ CFU/m L. A Tecan Sunrise microplate absorbance reader was used to measure the OD620 of each well before and after 20 h incubation at 37° C. MIC values were recorded as the lowest compound concentration at which no visible growth was observed after this incubation period.

Determination of MBC Values

When a MIC was observed, 5 $\mu$L of each well within the corresponding dilution series that contained compound at a concentration greater than or equal to the MIC was spotted onto TSA with 5% sheep blood. Following 24 h incubation of these subcultures at 37° C., MBC values were recorded as the lowest compound concentration at which no viable colonies were observed.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

REFERENCES

1. Murray, C. K., et al., *Bacteriology of war wounds at the time of injury*. Mil Med, 2006. 171(9): p. 826-9.
2. Murray, C. K., et al., *Methicillin-resistant Staphylococcus aureus in wound cultures recovered from a combat support hospital in Iraq*. J Trauma, 2010. 69 Suppl 1: p. S102-8.
3. Johnson, E. N., et al., *Infectious complications of open type III tibial fractures among combat casualties*. Clin Infect Dis, 2007. 45(4): p. 409-15.
4. Theuretzbacher, U. and J. H. Toney, *Nature's clarion call of antibacterial resistance: are we listening?* Curr Opin Investig Drugs, 2006. 7(2): p. 158-66.
5. D'Costa, V. M., et al., *Sampling the antibiotic resistome*. Science, 2006. 311(5759): p. 374-7.
6. Dorsett, Y. and T. Tuschl, *siRNAs: applications in functional genomics and potential as therapeutics*. Nat Rev Drug Discov, 2004. 3(4): p. 318-29.
7. Hermann, T. and E. Westhof, *Rational drug design and high-throughput techniques for RNA targets*. Comb Chem High Throughput Screen, 2000. 3(3): p. 219-34.
8. Brodersen, D. E., et al., *The structural basis for the action of the antibiotics tetracycline, pactamycin, and hygromycin B on the 30S ribosomal subunit*. Cell, 2000. 103(7): p. 1143-54.
9. Carter, A. P., et al., *Functional insights from the structure of the 30S ribosomal subunit and its interactions with antibiotics*. Nature, 2000. 407(6802): p. 340-8.
10. Hansen, J. L., et al., *The structures of four macrolide antibiotics bound to the large ribosomal subunit*. Mol Cell, 2002. 10(1): p. 117-28.

11. Pioletti, M., et al., *Crystal structures of complexes of the small ribosomal subunit with tetracycline, edeine and IF3*. EMBO J, 2001. 20(8): p. 1829-39.
12. Schlunzen, F., et al., *Structural basis for the interaction of antibiotics with the peptidyl transferase centre in eubacteria*. Nature, 2001. 413(6858): p. 814-21.
13. Vicens, Q. and E. Westhof, *RNA as a drug target: the case of aminoglycosides*. Chembiochem, 2003. 4(10): p. 1018-23.
14. Ennifar, E., et al., *HIV-1 RNA dimerization initiation site is structurally similar to the ribosomal A site and binds aminoglycoside antibiotics*. J Biol Chem, 2003. 278(4): p. 2723-30.
15. Eubank, T. D., et al., *Inhibition of bacterial RNase P by aminoglycoside-arginine conjugates*. FEBS Lett, 2002. 511(1-3): p. 107-12.
16. von Ahsen, U. and H. F. Noller, *Footprinting the sites of interaction of antibiotics with catalytic group I intron RNA*. Science, 1993. 260(5113): p. 1500-3.
17. Corvaisier, S., V. Bordeau, and B. Felden, *Inhibition of transfer messenger RNA aminoacylation and trans-translation by aminoglycoside antibiotics*. J Biol Chem, 2003. 278(17): p. 14788-97.
18. Breaker, R. R., *Prospects for riboswitch discovery and analysis*. Mol Cell, 2011. 43(6): p. 867-79.
19. Roth, A. and R. R. Breaker, *The structural and functional diversity of metabolite-binding riboswitches*. Annu Rev Biochem, 2009. 78: p. 305-34.
20. Winkler, W. C. and R. R. Breaker, *Regulation of bacterial gene expression by riboswitches*. Annu Rev Microbiol, 2005. 59: p. 487-517.
21. Batey, R. T., S. D. Gilbert, and R. K. Montange, *Structure of a natural guanine-responsive riboswitch complexed with the metabolite hypoxanthine*. Nature, 2004. 432(7015): p. 411-5.
22. Mandal, M., et al., *Riboswitches control fundamental biochemical pathways in Bacillus subtilis and other bacteria*. Cell, 2003. 113(5): p. 577-86.
23. Serganov, A., et al., *Structural basis for discriminative regulation of gene expression by adenine-and guanine-sensing mRNAs*. Chem Biol, 2004. 11(12): p. 1729-41.
24. Serganov, A., et al., *Structural basis for gene regulation by a thiamine pyrophosphate-sensing riboswitch*. Nature, 2006. 441(7097): p. 1167-71.
25. Thore, S., M. Leibundgut, and N. Ban, *Structure of the eukaryotic thiamine pyrophosphate riboswitch with its regulatory ligand*. Science, 2006. 312(5777): p. 1208-11.
26. Sudarsan, N., J. E. Barrick, and R. R. Breaker, *Metabolite-binding RNA domains are present in the genes of eukaryotes*. RNA, 2003. 9(6): p. 644-7.
27. Green, N. J., F. J. Grundy, and T. M. Henkin, *The T box mechanism: tRNA as a regulatory molecule*. FEBS Lett, 2010. 584(2): p. 318-24.
28. Grundy, F. J. and T. M. Henkin, *tRNA as a positive regulator of transcription antitermination in B. subtilis*. Cell, 1993. 74(3): p. 475-82.
29. Gutierrez-Preciado, A., et al., *Biochemical features and functional implications of the RNA-based T-box regulatory mechanism*. Microbiol Mol Biol Rev, 2009. 73(1): p. 36-61.
30. Henkin, T. M., *Transcription termination control in bacteria*. Curr Opin Microbiol, 2000. 3(2): p. 149-53.
31. Henkin, T. M., *Riboswitch RNAs: using RNA to sense cellular metabolism*. Genes Dev, 2008. 22(24): p. 3383-90.
32. Garrity, D. B. and S. A. Zahler, *Mutations in the gene for a tRNA that functions as a regulator of a transcriptional attenuator in Bacillus subtilis*. Genetics, 1994. 137(3): p. 627-36.
33. Grundy, F. J., S. M. Rollins, and T. M. Henkin, *Interaction between the acceptor end of tRNA and the T box stimulates antitermination in the Bacillus subtilis tyrS gene: a new role for the discriminator base*. J Bacteriol, 1994. 176(15): p. 4518-26.
34. Gerdeman, M. S., T. M. Henkin, and J. V. Hines, *Solution structure of the Bacillus subtilis T-box antiterminator RNA: seven nucleotide bulge characterized by stacking and flexibility*. J Mol Biol, 2003. 326(1): p. 189-201.
35. Wang, J. and E. P. Nikonowicz, *Solution structure of the K-turn and Specifier Loop domains from the Bacillus subtilis tyrS T-box leader RNA*. J Mol Biol, 2011. 408(1): p. 99-117.
36. Gerdeman, M. S., T. M. Henkin, and J. V. Hines, *In vitro structure-function studies of the Bacillus subtilis tyrS mRNA antiterminator: evidence for factor-independent tRNA acceptor stem binding specificity*. Nucleic Acids Res, 2002. 30(4): p. 1065-72.
37. Rollins, S. M., F. J. Grundy, and T. M. Henkin, *Analysis of cis-acting sequence and structural elements required for antitermination of the Bacillus subtilis tyrS gene*. Mol Microbiol, 1997. 25(2): p. 411-21.
38. Winkler, W. C., et al., *The GA motif: an RNA element common to bacterial antitermination systems, rRNA, and eukaryotic RNAs*. RNA, 2001. 7(8): p. 1165-72.
39. Butcher, S. E. and J. M. Burke, *Structure-mapping of the hairpin ribozyme. Magnesium-dependent folding and evidence for tertiary interactions within the ribozyme-substrate complex*. J Mol Biol, 1994. 244(1): p. 52-63.
40. Leontis, N. B. and E. Westhof, *A common motif organizes the structure of multi-helix loops in 16 S and 23 S ribosomal RNAs*. J Mol Biol, 1998. 283(3): p. 571-83.
41. Nelson, A. R., T. M. Henkin, and P. F. Agris, *tRNA regulation of gene expression: interactions of an mRNA 5'-UTR with a regulatory tRNA*. RNA, 2006. 12(7): p. 1254-61.
42. Yousef, M. R., F. J. Grundy, and T. M. Henkin, *Structural transitions induced by the interaction between tRNA(Gly) and the Bacillus subtilis glyQS T box leader RNA*. J Mol Biol, 2005. 349(2): p. 273-87.
43. Li, P. T., C. Bustamante, and I. Tinoco, Jr., *Real-time control of the energy landscape by force directs the folding of RNA molecules*. Proc Natl Acad Sci USA, 2007. 104(17): p. 7039-44.
44. Li, P. T. and I. Tinoco, Jr., *Mechanical unfolding of two DIS RNA kissing complexes from HIV-1*. J Mol Biol, 2009. 386(5): p. 1343-56.
45. Smith, S. B., Y. Cui, and C. Bustamante, *Optical-trap force transducer that operates by direct measurement of light momentum*. Methods Enzymol, 2003. 361: p. 134-62.
46. Johnson, E. C., et al., *Application of NMR SHAPES screening to an RNA target*. J Am Chem Soc, 2003. 125(51): p. 15724-5.
47. Mayer, M. and T. L. James, *NMR-based characterization of phenothiazines as a RNA binding scaffold*. J Am Chem Soc, 2004. 126(13): p. 4453-60.
48. Zuker, M., *Mfold web server for nucleic acid folding and hybridization prediction*. Nucleic Acids Res, 2003. 31(13): p. 3406-15.

49. Jeener, J. M., B. H.; Bachmann, P.; Ernst, R. R., *Investigation of exchange processes by two-dimensional NMR spectroscopy*. Journal of Chemical Physics, 1979. 71(11): p. 4546-4553
50. Bothner-By, A. A., Stephens, R. L., Lee, J., Warren, C. D., Jeanloz, R. W., *Structure determination of a tetrasaccharide: transient nuclear Overhauser effects in the rotating frame*. J. Am. Chem. Soc., 1984. 106(3): p. 811-813.
51. Bax, A., and Summers, M. F., *'H and 13C Assignments from Sensitivity-Enhanced Detection of Heteronuclear Multiple-Bond Connectivity by 2D Multiple Quantum NMR*. J. Am. Chem. Soc., 1986. 108: p. 2093-2094.
52. Piotto, M., V. Saudek, and V. Sklenar, *Gradient-tailored excitation for single-quantum NMR spectroscopy of aqueous solutions*. J Biomol NMR, 1992. 2(6): p. 661-5.
53. Delaglio, F., et al., *NMRPipe: a multidimensional spectral processing system based on UNIX pipes*. J Biomol NMR, 1995. 6(3): p. 277-93.
54. Johnson, B. A., and Blevins, R. A., *NMR View: A computer program for the visualization and analysis of NMR data*. Journal of Biomolecular NMR, 1994. 4: p. 603-614.
55. Guntert, P., C. Mumenthaler, and K. Wuthrich, *Torsion angle dynamics for NMR structure calculation with the new program DYANA*. J Mol Biol, 1997. 273(1): p. 283-98.
56. Case, D. A., Pearlman, D. A., Caldwell, J. W., Cheatham, T. E., Wang, J., Ross, W. S., C. L. Simmerling, Darden, T. A., Merz, K. M., Stanton, R. V., Cheng, A. L., Vincent, J. J., Crowley, M., and V. Tsui, Gohlke, H., Radmer, R. J., Duan, Y., Pitera, J., Massova, I., Seibel, G. L., Singh, U. C., Weiner, P. K., and Kollman, P. A. (2002) *AMBER 7 manual*. UCSF, San Francisco
57. Lu, K., et al., *NMR detection of structures in the HIV-1 5'-leader RNA that regulate genome packaging*. Science, 2011. 334(6053): p. 242-5.
58. Cerrone-Szakal, A. L., et al., *Mechanistic characterization of the HDV genomic ribozyme: the cleavage site base pair plays a structural role in facilitating catalysis*. RNA, 2008. 14(9): p. 1746-60.
59. Yu, E. and D. Fabris, *Direct probing of RNA structures and RNA-protein interactions in the HIV-1 packaging signal by chemical modification and electrospray ionization fourier transform mass spectrometry*. J Mol Biol, 2003. 330(2): p. 211-23.
60. Young, M. M., et al., *High throughput protein fold identification by using experimental constraints derived from intramolecular cross-links and mass spectrometry*. Proc Natl Acad Sci USA, 2000. 97(11): p. 5802-6.
61. Babendure, J. R., S. R. Adams, and R. Y. Tsien, *Aptamers switch on fluorescence of triphenylmethane dyes*. J Am Chem Soc, 2003. 125(48): p. 14716-7.
62. Lemay, J. F. and D. A. Lafontaine, *Core requirements of the adenine riboswitch aptamer for ligand binding*. RNA, 2007. 13(3): p. 339-50.
63. Grundy, F. J. and T. M. Henkin, *Kinetic analysis of tRNA-directed transcription antitermination of the Bacillus subtilis glyQS gene in vitro*. J Bacteriol, 2004. 186(16): p. 5392-9.
64. Chen, L. J. and E. M. Orozco, Jr., *Recognition of prokaryotic transcription terminators by spinach chloroplast RNA polymerase*. Nucleic Acids Res, 1988. 16(17): p. 8411-31.
65. Christiansen, J., *The 9S RNA precursor of Escherichia coli 5S RNA has three structural domains: implications for processing*. Nucleic Acids Res, 1988. 16(15): p. 7457-76.
66. Jeng, S. T., J. F. Gardner, and R. I. Gumport, *Transcription termination by bacteriophage T7 RNA polymerase at rho-independent terminators*. J Biol Chem, 1990. 265(7): p. 3823-30.
67. Chamberlin, M., et al., *Isolation of bacterial and bacteriophage RNA polymerases and their use in synthesis of RNA in vitro*. Methods Enzymol, 1983. 101: p. 540-68.
68. Chamberlin, M. J., et al., *A quantitative assay for bacterial RNA polymerases*. J Biol Chem, 1979. 254(20): p. 10061-9.
69. Golomb, M. and M. Chamberlin, *Characterization of T7-specific ribonucleic acid polymerase. IV. Resolution of the major in vitro transcripts by gel electrophoresis*. J Biol Chem, 1974. 249(9): p. 2858-63.
70. Deora, R. and T. K. Misra, *Purification and characterization of DNA dependent RNA polymerase from Staphylococcus aureus*. Biochem Biophys Res Commun, 1995. 208(2): p. 610-6.
71. Rao, L., R. K. Karls, and M. J. Betley, *In vitro transcription of pathogenesis-related genes by purified RNA polymerase from Staphylococcus aureus*. J Bacteriol, 1995. 177(10): p. 2609-14.
72. Grigg J C, Chen Y, Grundy F J, Henkin T M, Pollack L, Ke A. (2013) *T-box RNA decodes both the information content and geometry of tRNA to affect gene expression*. Proc Natl Acad Sci USA. 110:7240-5.
73. Wang J, Nikonowicz EP. (2011) Solution Structure of the K-Turn and Specifier Loop Domains from the *Bacillus subtilis* tyrS T-Box Leader RNA. J Mol Biol. 408:99-117.
74. Biemer J J. (1973) Antimicrobial susceptibility testing by the Kirby-Bauer disc diffusion method. Ann Clin Lab Sci. 3:135-40.
75. Blount K F, Breaker R R. (2006) Riboswitches as antibacterial drug targets. Nat Biotechnol. 24:1558-64.
76. Deigan K E, Ferré-D'Amaré A R. (2011) Riboswitches: discovery of drugs that target bacterial gene-regulatory RNAs. Acc Chem Res. 44:1329-38.
77. Andrews J M. (2001) Determination of minimum inhibitory concentrations. J Antimicrob Chemother. 48 Suppl 1:5-16.
78. Jorgensen J H, Ferraro M J. (2009) Antimicrobial susceptibility testing: a review of general principles and contemporary practices. Clin Infect Dis. 49:1749-55.

The invention claimed is:
1. A method for inhibiting the growth of Gram-positive bacteria comprising contacting said bacteria with a compound of Formula (II):

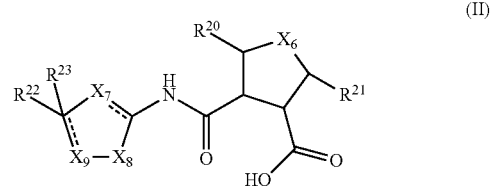

or a pharmaceutically acceptable salt thereof, wherein:
$X_6$ is selected from $CH_2$ and $-CR^{24}=CR^{25}-$;
$X_7$ is selected from nitrogen and $CH_2$;
$X_8$ is selected from sulfur and $CH_2$;
$X_9$ is selected from $CR^{24}$ and $-CHR^{24}-CHR^{25}-$;
represents a single or double bond, wherein both instances of $=\!=\!=$ are double bonds when $X_7$ and $X_8$ are nitrogen and sulfur, respectively, and both instances $=\!=\!=$ are single bonds when $X_7$ and $X_8$ are both $CH_2$;

$R^{20}$ and $R^{21}$ are individually selected from hydrogen and $C_{1-3}$ alkyl, or $R^{20}$ and $R^{21}$, taken together, represent a —$CH_2$—$CH_2$— linker;

$R^{22}$ is selected from hydrogen, $C_{1-3}$ alkyl, a 5-membered aryl or heteroaryl ring or 6-membered heteroaryl ring wherein said 5-membered aryl or heteroaryl ring or 6-membered heteroaryl ring is optionally substituted with 1, 2, or 3 substituents individually selected from $C_{1-6}$ alkyl and halogen, and a 6-membered aryl ring optionally substituted only with a single $C_{1-6}$ alkyl substituent;

$R^{23}$ is absent or is selected from hydrogen and $C_{1-3}$ alkyl; and $R^{24}$ and $R^{25}$ are individually selected from hydrogen and $C_{1-3}$ alkyl; and wherein the bacteria are contacted with a compound of Formula II or a pharmaceutical salt thereof in solution at a concentration of 1 milligram or less per milliliter.

2. A method for the treatment of a Gram-positive bacterial infection in an individual comprising administering a compound of Formula (II):

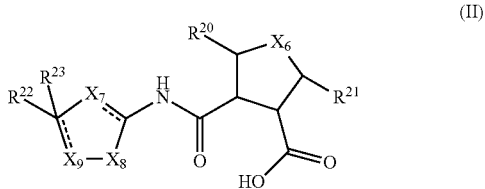

(II)

or a pharmaceutically acceptable salt thereof, wherein:
$X_6$ is selected from $CH_2$ and —$CR^{24}$=$CR^{25}$—;
$X_7$ is selected from nitrogen and $CH_2$;
$X_8$ is selected from sulfur and $CH_2$;
$X_9$ is selected from $CR^{24}$ and —$CHR^{24}$—$CHR^{25}$—;
⁼ represents a single or double bond, wherein both instances of ⁼ are double bonds when $X_7$ and $X_8$ are nitrogen and sulfur, respectively, and both instances ⁼ are single bonds when $X_7$ and $X_8$ are both $CH_2$;

$R^{20}$ and $R^{21}$ are individually selected from hydrogen and $C_{1-3}$ alkyl, or $R^{20}$ and $R^{21}$, taken together, represent a —$CH_2$—$CH_2$— linker;

$R^{22}$ is selected from hydrogen, $C_{1-3}$ alkyl, a 5-membered aryl or heteroaryl ring or 6-membered heteroaryl ring wherein said 5-membered aryl or heteroaryl ring or 6-membered heteroaryl ring is optionally substituted with 1, 2, or 3 substituents individually selected from $C_{1-6}$ alkyl and halogen, and a 6-membered aryl ring optionally substituted only with a single $C_{1-6}$ alkyl substituent;

$R^{23}$ is absent or is selected from hydrogen and $C_{1-3}$ alkyl; and $R^{24}$ and $R^{25}$ are individually selected from hydrogen and $C_{1-3}$ alkyl; and wherein the compound of Formula II or a pharmaceutically acceptable salt thereof is administered in a dose of less than 300 milligrams per day.

3. The method of claim 1, wherein the Gram-positive bacteria is *Staphylococcus aureus, Bacillus subtilis, Streptococcus pneumoniae*, or *Bacillus cereus*.

4. The method of claim 2, wherein the Gram-positive bacteria is *Staphylococcus aureus, Bacillus subtilis, Streptococcus pneumoniae*, or *Bacillus cereus*.

5. The method of claim 1, wherein the compound further comprises a pharmaceutically acceptable excipient.

6. The method of claim 2, wherein the compound further comprises a pharmaceutically acceptable excipient.

7. The method of claim 3, wherein the compound further comprises a pharmaceutically acceptable excipient.

8. The method of claim 4, wherein the compound further comprises a pharmaceutically acceptable excipient.

9. The method of claim 1, wherein the bacteria are contacted with a compound of Formula II or a pharmaceutical salt thereof in solution at a concentration of 500 micrograms or less per milliliter.

10. The method of claim 1, wherein the bacteria are contacted with a compound of Formula II or a pharmaceutical salt thereof in solution at a concentration of 150 micrograms or less per milliliter.

11. The method of claim 2, wherein the compound of Formula II or a pharmaceutically acceptable salt thereof is administered in a dose of 100 milligrams or more and less than 300 milligrams per day.

12. The method of claim 2, wherein the compound of Formula II or a pharmaceutically acceptable salt thereof is administered in a dose of 1 milligram or more and less than 100 milligrams per day.

13. A method for inhibiting the growth of Gram-positive bacteria comprising contacting said bacteria with a compound of Formula (II):

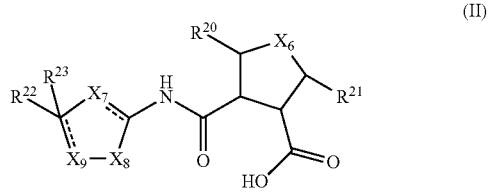

(II)

or a pharmaceutically acceptable salt thereof, wherein:
$X_6$ is $CH_2$;
$X_7$ is nitrogen;
$X_8$ is sulfur;
$X_9$ is $CR^{24}$ and $R^{24}$ is $C_{1-3}$ alkyl;
both instances of ⁼ are double bonds;
$R^{20}$ and $R^{21}$, taken together, represent a —$CH_2$—$CH_2$— linker;
$R^{22}$ is 4-isopropylphenyl; and $R^{23}$ is absent.

14. The method of claim 13, wherein the Gram-positive bacteria is *Staphylococcus aureus, Bacillus subtilis, Streptococcus pneumoniae*, or *Bacillus cereus*.

15. The method of claim 13, wherein the compound further comprises a pharmaceutically acceptable excipient.

16. The method of claim 14, wherein the compound further comprises a pharmaceutically acceptable excipient.

17. The method of claim 13, wherein $R_{24}$ is —$CH_3$.

* * * * *

UNITED STATES PATENT AND TRADEMARK OFFICE
CERTIFICATE OF CORRECTION

PATENT NO. : 10,266,527 B2
APPLICATION NO. : 14/907138
DATED : April 23, 2019
INVENTOR(S) : Paul F. Agris Page 1 of 1

It is certified that error appears in the above-identified patent and that said Letters Patent is hereby corrected as shown below:

In the Claims

Column 36, Line 64: Claim 1, Delete "represents" and insert --  represents --

Signed and Sealed this
Eleventh Day of June, 2019

Andrei Iancu
*Director of the United States Patent and Trademark Office*